US008464716B2

(12) United States Patent
Kuehne et al.

(10) Patent No.: US 8,464,716 B2
(45) Date of Patent: Jun. 18, 2013

(54) DIFFERENTIAL AIR PRESSURE SYSTEMS

(75) Inventors: Eric Richard Kuehne, Los Gatos, CA (US); Mark Alan Shughart, Palo Alto, CA (US); Sean T. Whalen, Mountain View, CA (US); Douglas Frank Schwandt, Palo Alto, CA (US); Robert T. Whalen, Los Altos, CA (US)

(73) Assignee: AlterG, Inc., Fremont, CA (US)

( * ) Notice: Subject to any disclaimer, the term of this patent is extended or adjusted under 35 U.S.C. 154(b) by 466 days.

(21) Appl. No.: 12/778,747

(22) Filed: May 12, 2010

(65) Prior Publication Data

US 2011/0120567 A1 May 26, 2011

Related U.S. Application Data

(60) Provisional application No. 61/178,901, filed on May 15, 2009.

(51) Int. Cl.
*A61M 11/00* (2006.01)

(52) U.S. Cl.
USPC .................. 128/205.26; 128/202.12; 601/11; 601/35; 601/19; 482/54

(58) Field of Classification Search
USPC ................. 601/5–11, 23, 25, 35; 128/202.12, 128/205.26; 482/54; 600/19
See application file for complete search history.

(56) References Cited

U.S. PATENT DOCUMENTS

| | | | |
|---|---|---|---|
| 44,196 | A | 9/1864 | Jones |
| 54,530 | A | 5/1866 | Hadfield |
| 60,883 | A | 1/1867 | Hadfield |
| 72,631 | A | 12/1867 | Hadfield |
| 100,867 | A | 3/1870 | Curran |
| 871,074 | A | 11/1907 | Stockton |
| 3,768,467 | A | 10/1973 | Jennings |
| 4,149,712 | A | 4/1979 | Murphy |
| 4,257,407 | A | 3/1981 | Macchi |
| 4,343,302 | A | 8/1982 | Dillon |
| 4,411,422 | A | 10/1983 | Solloway |
| 4,509,513 | A | 4/1985 | Lasley |
| 4,536,163 | A | 8/1985 | Schnirch et al. |
| 4,576,376 | A | 3/1986 | Miller |
| 4,621,621 | A | 11/1986 | Marsalis |

(Continued)

FOREIGN PATENT DOCUMENTS

| | | | |
|---|---|---|---|
| CN | 2208414 | Y | 9/1995 |
| JP | 59-002993 | | 1/1984 |

(Continued)

OTHER PUBLICATIONS

Whalen et al.; U.S. Appl. No. 13/543,566 entitled "Systems, Methods and Apparatus for Calibrating Differential Air Pressure Devices," filed Jul. 6, 2012.

(Continued)

*Primary Examiner* — Steven Douglas
(74) *Attorney, Agent, or Firm* — Shay Glenn LLP

(57) ABSTRACT

Described herein are various embodiments of differential air pressure systems and methods of using such systems. The differential air pressure system may comprise a chamber configured to receive a portion of a user's lower body and to create an air pressure differential upon the user's body. The differential air pressure system may further comprise a user seal that seal the pressure chamber to the user's body. The height of the user seal may be adjusted to accommodate users with various body heights.

18 Claims, 30 Drawing Sheets

U.S. PATENT DOCUMENTS

| | | | |
|---|---|---|---|
| 4,712,788 | A | 12/1987 | Gaudreau, Jr. |
| 4,776,581 | A | 10/1988 | Shepherdson |
| 4,805,601 | A | 2/1989 | Eischen, Sr. |
| 4,934,694 | A | 6/1990 | McIntosh |
| 4,959,047 | A | 9/1990 | Tripp, Jr. |
| 4,974,829 | A | 12/1990 | Gamow et al. |
| 5,029,579 | A | 7/1991 | Trammel |
| 5,133,339 | A | 7/1992 | Whalen et al. |
| 5,242,339 | A | 9/1993 | Thornton |
| 5,356,361 | A | 10/1994 | Watenpaugh |
| 5,368,532 | A | 11/1994 | Farnet |
| 5,398,678 | A | 3/1995 | Gamow |
| 5,571,062 | A | 11/1996 | Saganovsky |
| 5,702,323 | A | 12/1997 | Poulton |
| 5,738,612 | A | 4/1998 | Tsuda |
| 5,799,652 | A | 9/1998 | Kotliar |
| 5,860,857 | A | 1/1999 | Wasastjerna et al. |
| 5,921,892 | A | 7/1999 | Easton |
| 6,027,464 | A | 2/2000 | Dahlquist |
| 6,033,344 | A | 3/2000 | Trulaske et al. |
| 6,042,537 | A | 3/2000 | Kaiser |
| 6,332,354 | B1 | 12/2001 | Lalor et al. |
| 6,482,128 | B1 | 11/2002 | Michalow |
| 6,527,678 | B1 | 3/2003 | Wang et al. |
| 6,539,946 | B2 | 4/2003 | Weyergans |
| 6,565,624 | B2 | 5/2003 | Kutt et al. |
| 6,666,831 | B1 | 12/2003 | Edgerton et al. |
| D495,384 | S | 8/2004 | Rolfes |
| 6,783,482 | B2 | 8/2004 | Oglesby et al. |
| 6,905,459 | B2 | 6/2005 | Humphries, Jr. |
| 7,141,007 | B2 | 11/2006 | Egger |
| 7,556,040 | B2 | 7/2009 | Meyer et al. |
| 7,591,795 | B2 | 9/2009 | Whalen et al. |
| 7,837,597 | B2 | 11/2010 | Reyes et al. |
| 7,850,629 | B2 | 12/2010 | Ravikumar |
| 2003/0032904 | A1 | 2/2003 | Egger |
| 2004/0238285 | A1 | 12/2004 | Stokes |
| 2005/0075680 | A1 | 4/2005 | Lowry et al. |
| 2005/0239613 | A1 | 10/2005 | Colombo et al. |
| 2006/0009333 | A1 | 1/2006 | Wang |
| 2006/0190051 | A1 | 8/2006 | Gerber et al. |
| 2007/0054783 | A1 | 3/2007 | Egger |
| 2009/0014004 | A1 | 1/2009 | Whalen et al. |
| 2009/0018571 | A1 | 1/2009 | Whalen et al. |
| 2009/0082700 | A1 | 3/2009 | Whalen et al. |
| 2009/0255531 | A1 | 10/2009 | Johnson et al. |
| 2010/0000547 | A1 | 1/2010 | Johnson et al. |
| 2011/0098157 | A1 | 4/2011 | Whalen et al. |
| 2011/0098615 | A1 | 4/2011 | Whalen et al. |

FOREIGN PATENT DOCUMENTS

| | | | |
|---|---|---|---|
| JP | 63109878 | A | 5/1988 |
| JP | 5-500760 | | 2/1993 |
| JP | 1022334 | | 10/1998 |
| JP | 2001-112886 | | 4/2001 |
| JP | 2002-360644 | | 12/2002 |
| JP | 1395000 | | 8/2010 |
| WO | WO 2006/061834 | A2 | 6/2006 |
| WO | WO 2009/051765 | A1 | 4/2009 |

OTHER PUBLICATIONS

Hargens et al.; Lower body negative pressure to provide load bearing in space; Aviat Space Environ Med; 62(10); pp. 934-937; Oct. 1991.

Whalen et al.; Design U.S. App. No. 29/337,097 entitled “Adjustable Positive Pressure Support System,” filed May 14, 2009.

Kuehne et al.; U.S. Appl. No. 13/423,124 entitled “Differential air pressure systems and methods of using and calibrating such systems for mobility impaired users,” filed Mar. 16, 2012.

“Feedback Control System;” The Encyclopedia Americana International Edition; pp. 82-84; Dec. 2003.

Kawai et al.; Rehabilitation apparatus for treadmill walking using lower body positive pressue (Japanese & English abstracts); Aerospace and Environmental Medicine; vol. 44; No. 4; (month unavailable) 2007.

Vacu Well Wellness & Beauty; Company History and Vacu Well Power Professional treadmill specifications; printed from website (http://www.vacuwell.com); 3 pgs.; printed Apr. 4, 2012.

DIFFERENTIAL AIR PRESSURE SYSTEMS

CROSS-REFERENCE TO RELATED APPLICATIONS

This application claims priority to U.S. Provisional Application Ser. No. 61/178,901 filed on May 15, 2009 and titled "DIFFERENTIAL AIR PRESSURE SYSTEMS," the entirety of which is hereby incorporated by reference in its entirety.

FIELD

The present invention generally relates to differential air pressure systems of methods of using such systems.

BACKGROUND

Methods of counteracting gravitational forces on the human body have been devised for therapeutic applications as well as physical training. One way to counteract the effects of gravity is to suspend a person using a body harness to reduce ground impact forces. However, harness systems may cause pressure points that may lead to discomfort and sometimes even induce injuries. Another approach to counteract the gravity is to submerge a potion of a user's body into a water-based system and let buoyancy provided by the water offset gravity. However, the upward supporting force provided by such water-based systems distributes unevenly on a user's body, varying with the depth of the user's body from the water surface. Moreover, the viscous drag of the water may substantially alter the muscle activation patterns of the user.

BRIEF SUMMARY

Described herein are various embodiments of differential air pressure systems and methods of using such systems. The differential air pressure system may comprise a chamber configured to receive a portion of a user's lower body and to create an air pressure differential upon the user's body. The differential air pressure system may further comprise a user seal that seal the pressure chamber to the user's body. The height of the user seal may be adjusted to accommodate users with various body heights.

In one example, a differential air pressure system is provided, comprising a positive pressure chamber with a seal interface configured to receive a portion of a user's body and form a seal between the user's body and the chamber, and a height adjustment assembly attached to the chamber adjacent to the seal interface, and a control panel attached to the height adjustment assembly. The positive pressure chamber may comprise at least one or a plurality of transparent panels, and/or a slip resistant panel. The slip resistant panel may be adjacent to the seal interface. The height adjustment assembly may comprise two movable ends located within two corresponding adjustment posts, wherein each movable end may comprise at least two rollers. In some further examples, a first roller may be orthogonally or oppositely oriented with respect to a second roller, and in other examples, may comprise three rollers, with a first roller on a first surface, a second roller located on an opposite surface from the first surface, and a third roller located on an orthogonal surface from the first surface or opposite surface. The each movable end may also comprise at least one movable braking pad, which may or may not be configured to actuate by tilting the height adjustment assembly. The height adjustment assembly may comprise a locking mechanism, which may be horizontally, vertically, rotationally actuated, pull or push-actuated. The locking mechanism may be a pin latch locking mechanism configured to lock the position of the user seal. The height adjustment mechanism may further comprises a counterbalancing system configured to at least partially offset the weight of the movable assembly, and in some examples, may be configured to balance the effective combined weight of the movable assembly and the positive pressure chamber. The counterbalancing system may comprise a weight located in at least one adjustment post. The system may also further comprise a platform attached to the chamber using a seal mechanism. The seal mechanism may be configured to increase sealing to the platform with increased pressure within chamber, and may comprise a foam member.

In another example, a differential air pressure system is provided, comprising a pressure chamber, and a vertically adjustable cantilevered frame having a first movable configuration and a second locked configuration wherein the second locked configuration is actuated by the inflation of the pressure chamber.

In another example, a method of adjusting a differential air pressure system is provided, comprising simultaneously raising a control panel and a pressure chamber using a counterbalanced height adjustment assembly. The method may further comprise tilting a cantilevered braking mechanism of the height adjustment assembly to engage or disengage the braking mechanism. In some examples, tilting of the cantilevered braking mechanism may be mechanically performed by inflating or deflating the pressure chamber.

In still another example, a method for using a differential air pressure system is provided, comprising increasing the pressure applied to a limb located in a pressure chamber sealably attached to a platform, and increasing the sealing of the pressure chamber and the platform corresponding to increasing the pressure applied to the limb.

BRIEF DESCRIPTION OF THE DRAWINGS

A better understanding of various features and advantages of the embodiments described herein may be obtained by reference to the following detailed description that sets forth illustrative examples and the accompanying drawings of which:

FIG. 4A is a frontal view of the pressure chamber; FIG. 4B is the top view of the chamber in FIG. 4A.

DETAILED DESCRIPTION

While embodiments have been described and presented herein, these embodiments are provided by way of example only. Variations, changes and substitutions may be made without departing from the embodiments. It should be noted that various alternatives to the exemplary embodiments described herein may be employed in practicing the embodiments. For all of the embodiments described herein, the steps of the methods need not to be performed sequentially.

Differential Air Pressure System

Differential air pressure (DAP) systems utilize changes in air pressure to provide positive or negative weight support for training and rehabilitation systems and programs. Various examples of DAP systems are described in International Patent Application Serial No. PCT/US2006/038591, filed on Sep. 28, 2006, titled "Systems, Methods and Apparatus for Applying Air Pressure on A Portion of the Body of An Individual," International Patent Application Serial No. PCT/US2008/011807, filed on Oct. 15 2008, entitled "Systems, Methods and Apparatus for Calibrating Differential Air Pressure Devices" and International Patent Application Serial No. PCT/US2008/011832, filed on Oct. 15, 2008, entitled "Systems, Methods and Apparatus for Differential Air Pressure Devices," all of which are hereby incorporated by reference in their entirety.

Figure 1:
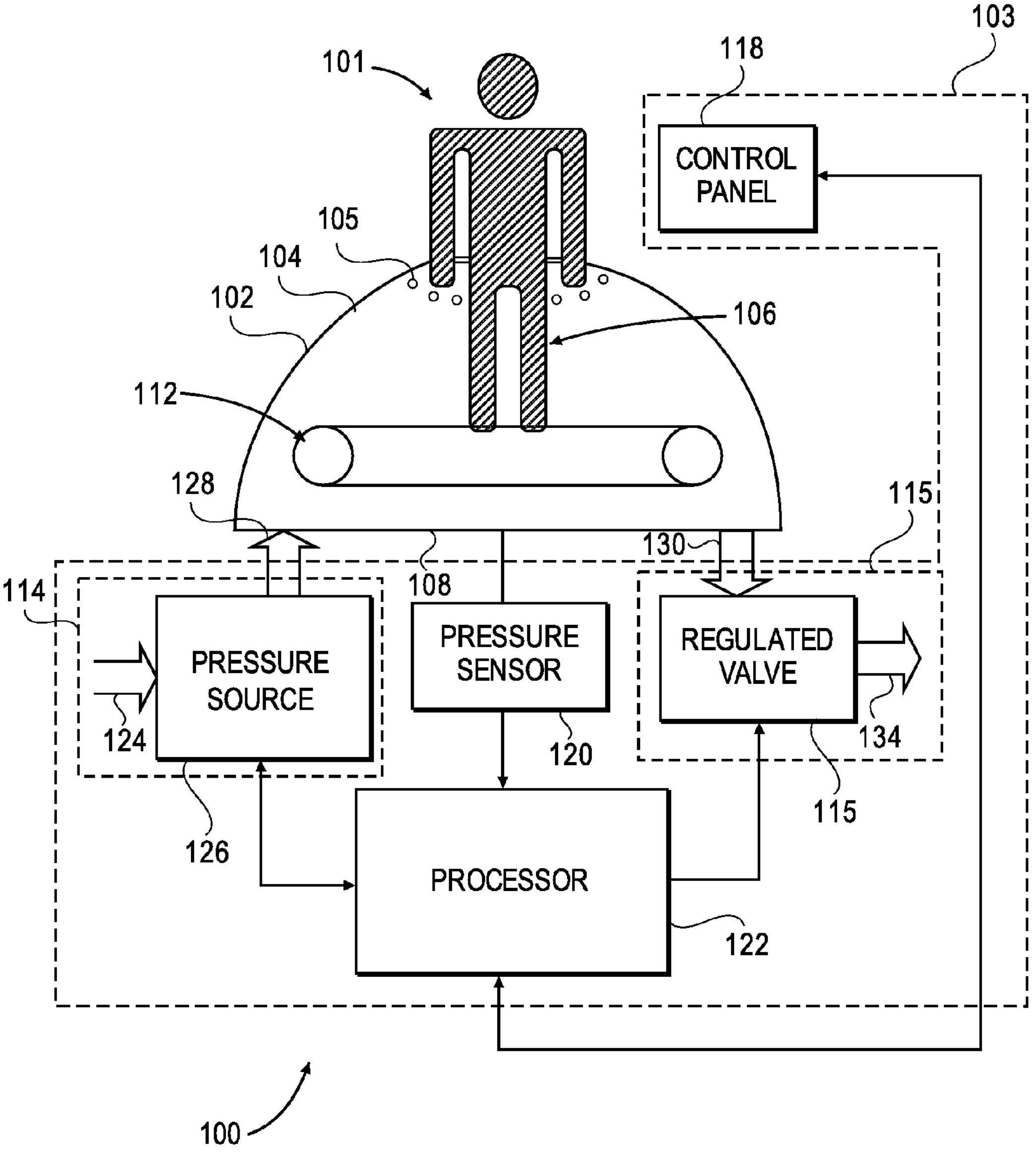
FIG. 1 is block diagram schematically illustrating one example of a differential air pressure system.

FIG. 1 schematically illustrates one example of a DAP system 100, comprising a sufficiently airtight chamber 102 which houses an optional exercise system 112. The chamber 102 includes a user seal 104 configured to receive a user 101 and to provide a sufficient airtight seal with the user's lower body 106. A pressure control system 103 is used to generate alter the pressure level ($P_2$) inside the chamber 102 relative to the ambient pressure outside the chamber ($P_1$). When a user positioned in the DAP system is sealed to the chamber 102 and the chamber pressure ($P_2$) is changed, the differential air pressure ($\Delta P=P_2-P_1$) between the lower body 106 of the user 101 inside chamber 102 and the upper body outside the chamber 102 generates a vertical force acting through the seal 104 and also directly onto the user's lower body 106. If the chamber pressure $P_2$ is higher than the ambient air pressure $P_1$, there will be an upward vertical force ($F_{air}$) that is proportionate to the product of the air pressure differential ($\Delta P$) and the cross-sectional area of the user seal 110. The upward force ($F_{air}$) may counteract gravitational forces, providing a partial body-weight-support that is proportional to the air pressure differential ($\Delta P$). This weight support may reduce ground impact forces acting on the joints, and/or reduce muscular forces needed to maintain posture, gait, or other neuromuscular activities, for example.

The chamber 102 may be attached to a platform or base 108 that supports the chamber 102 and the exercise machine 112. The exercise machine 112 may be at least partially or wholly housed within the chamber 102. Any of a variety of exercise machines may be used, e.g., a treadmill, a stepper machine, an elliptical trainer, a balance board, and the like. Other exercise machines that may be used also include seated equipment, such as a stationary bicycle or a rowing machine. Weight support with seated equipment may be used to facilitate physical therapy or exercise in non-ambulatory patients, including but not limited to patients with pressure ulcers or other friable skin conditions located at the ischial tuberosities or sacral regions, for example. The exercise system or machine 112, such a treadmill, may have one or more adjustment mechanisms (e.g. workload, height, inclination, and/or speed), which may be controlled or adjusted by the DAP system console, or may controlled separately. Other features, such as a heart rate sensor, may also be separately managed or integrated with the DAP console. Those of ordinary skill in the art will appreciate that the treadmill shown in FIG. 1 is not intended to be limiting and that other exercise machines can be used without departing from the concepts herein disclosed.

The chamber 102 may comprise a flexible chamber or enclosure, and may be made of any suitable flexible material. The flexible material may comprise a sufficiently airtight fabric or a material coated or treated with a material to resist or reduce air leakage. The material may also comprise slightly permeable or otherwise porous to permit some airflow, but sufficiently airtight to allow pressure to be increase inside the chamber. The chamber 102 may have a unibody design, or may comprise multi-panels and/or or multiple layers. In some variations, the chamber 102 may comprise one or more flexible portions and one or more semi-rigid or rigid portions. Rigid portions may be provided to augment the structural integrity of the chamber 102, and/or to control the expansion or collapse of the chamber 102. The rigid portions may have a fixed position, e.g. affixed to a fixed platform or rail, or may comprise a rigid section, panel, or rod (or other reinforcement member) surrounded by flexible material which changes position with inflation or deflation. Examples of such panels or materials are described in greater detail below. In other examples, the chamber 102 may comprise a frame or other structures comprising one or more elongate members, disposed either inside and/or outside of a flexible enclosure, or integrated into the enclosure material(s). A rigid enclosure or a rigid portion may be made of any suitable rigid material, e.g., wood, plastic, metal, etc.

The user seal 104 of the chamber 102 may comprise an elliptical, circular, polygonal or other shape and may be made from flexible materials to accommodate various shapes and/or sizes of waistline of individual user 101. The user seal 104 may be adjustable to accommodate persons of different body sizes and/or shapes, or configured for a particular range of sizes or body forms. Non-limiting examples of the various user seal designs include the use of zippers, elastic bands, a cinchable member (e.g., drawstrings or laces), high friction materials, cohesive materials, magnets, snaps, buttons, VELCRO™, and/or adhesives, and are described in greater detail in PCT Appl. No. PCT/US2006/038591, PCT/US2008/011807, and PCT/US2008/011832, which were previously referenced and incorporated by reference. In some examples, the user seal 104 may comprise a separate pressure structure or material that may be removably attached to the chamber 102. For example, the user seal may comprise a waistband or belt with panels or a skirt, or a pair of shorts or pants. One or more of above listed attaching mechanisms may be used to attach such separate pressure closure to the user's body in a sufficiently airtight manner. The seal 104 may be breathable and/or washable. In some embodiments, the seal 104 may seal up to the user's chest, and in some variations the seal 104 may extend from the user's waist region up to the chest.

The user seal 104 and/or chamber 102 may comprise a plurality of openings 105. The openings 105 may be used to alter the temperature and/or humidity in the chamber or the torso region of the user, and/or may be configured to control the pressure distribution about the waist or torso of the user 101. For example, openings positioned in front of the user's torso may prevent pressure from building up around the user's stomach due to ballooning of the flexible waist seal under pressure. The openings may comprise regions of non-airtight fabrics, or by forming larger openings in the wall of the chamber 102. The openings may have a fixed configuration (e.g. fixed effective opening size) or a variable configuration (e.g. adjustable effective opening size or flow). The openings may comprise a port or support structure, which may provide reinforcement of the patency and/or integrity of the opening. The port or support structure may also comprise a valve or shutter mechanism to provide a variable opening configuration. These openings may be manually adjustable or automatically adjustable by a controller. In some variations, the openings with a variable configuration may be independently controlled.

As mentioned previously, a pressure control system 103 may be used to manage the pressure level within the chamber 102. Various examples of pressure control systems are described in PCT Appl. No. PCT/US2006/038591, PCT/US2008/011807, and PCT/US2008/011832, which were previously incorporated by reference. As illustrated in FIG. 1, the pressure control system 103 may comprise one or more pressure sensors 120, a processor 122, and a pressure source 114. The pressure source 114 may be pump, a blower or any type of device that may introduce pressurized gas into the chamber 102. In the particular example in FIG. 1, the pressure source 114 comprises a compressor or blower system 126, which further comprises an inlet port 124 for receiving a gas (e.g., air), an outlet port 128 to the chamber 102. The compressor or blower system 126 may comprise a variable pump or fan speed that may be adjusted to control the airflow or pressure to the chamber 102. In other examples, the pressure control system may be located within the chamber, such that the inlet port of the system is located about a wall of the chamber and where the outlet port of the system is located within the chamber.

In some variations, the DAP system 100 may further comprise a chamber venting system 116. The venting system 116 may comprise an inlet port 130 to receive gas or air from the chamber 102, one or more pressure regulating valves 132, and an outlet port 134. The pressure regulating valve 132 and its outlet port 134 may be located outside the chamber 102, while the inlet port 130 may be located in a wall of the chamber 102 (or base). In other variations, the pressure regulating valve and the inlet port may be located within the chamber while the outlet port is located in a wall of the chamber or base. The valve 132 may be controlled by the pressure control system 103 to reduce pressures within the chamber 102, either in combination with the control of the pressure source 114 (e.g. reducing the flow rate of the blower 126) and/or in lieu of control of the pressure source 114 (e.g. where the pressure source is an unregulated pressure source). The valve 132 may also be configured for use as a safety mechanism to vent or de-pressurize the chamber 102, during an emergency or system failure, for example. In other variations, a separate safety valve (not shown) with the pressure regulating valve. The separate safety may be configured to with a larger opening or higher flow rate than the pressure regulating valve.

In some examples, the processor 122 may be configured to control and/or communicate with the pressure source 114, a chamber pressure sensor 120, the exercise system 112 and/or a user interface system (e.g., a user control panel) 118. The communication between the processor 122 and each of above referenced components of the control system 103 may be one-way or two-way. The processor 122 may receive any of a variety of signals to or from pressure source 114, such as on/off status and temperature of the pressure source 114, the gas velocity/temperature at the inlet port 124 and/or the outlet port 128. The processor 122 may also send or receive signals from the control panel 118, including a desired pressure within the chamber 102, a desired percentage of body weight of the individual to be offset, an amount of weight to offset the user's body weight, and/or a pain level. The processor 122 may also receive input from the pressure sensor 120 corresponding to the pressure level within the chamber 102. Based on its input from any of above described sources, the processor 122 may send a drive signal to the pressure source 114 (or pressure regulating valve 115) to increase or decrease the airflow to the chamber 102 so as to regulate the pressure within chamber 102 to the desired level. In some variations, the desired pressure level may be a pre-set value, and in other variations may be a value received from the control panel 118 or derived from information received from the user, e.g., via the control panel 118, or other sensors, including weight sensors, stride frequency sensors, heart rate sensors, gait analysis feedback such as from a camera with analysis software, or ground reaction force sensors, etc. The processor 122 may send signals to change one or more parameters of the exercise system 112 based on the pressure reading of the chamber 102 from the pressure sensor 120 and/or user instructions from the control panel 118.

The control panel 118 may also be used to initiate or perform one or more calibration procedures. Various examples of calibration procedures that may be used are described in International Patent Application Serial No. PCT/US2006/038591, filed on Sep. 28, 2006, titled "Systems, Methods and Apparatus for Applying Air Pressure on A Portion of the Body of An Individual," International Patent Application Serial No. PCT/US2008/011807, filed on Oct. 15, 2008, entitled "Systems, Methods and Apparatus for Calibrating Differential Air Pressure Devices" and International Patent Application Serial No. PCT/US2008/011832, which were previously incorporated by reference in their entirety. Briefly, the pressure control system 103 may apply a series or range of pressures (or airflow rates) to a user sealed to the DAP system 100 while measuring the corresponding weight or ground reaction force of the user. Based upon the paired values, the pressure control system can generate a calibrated interrelationship between pressure and the relative weight of a user, as expressed as a percentage of normal body weight or gravity. In some examples, the series or range of pressures may be a fixed or predetermined series or range, e.g. the weight of the user is measured for each chamber pressure from X mm Hg to Y mm Hg in increments of Z mm Hg. X may be in the range of about 0 to about 100 or more, sometimes about 0 to about 50, and other times about 10 to about 30. Y may be in the range of about 40 to about 150 or more, sometimes about 50 to about 100, and other times about 60 to about 80. Z may be in the range of about 1 to about 30 or more, sometimes about 5 to about 20 and other times about 10 to about 15. The fixed or predetermined series or range may be dependent or independent of the user's weight or mass, and/or other factors such as the user's height or the elevation above sea level. In one specific example, a user's baseline weight is measured at atmospheric pressure and then X, Y and/or Z are determined based upon the measured weight. In still another example, one or more measurements of the user's static ground reaction force may be made at one or more non-atmospheric pressures and then escalated to a value Y determined during the calibration process. In some examples, the pressure control system may also include a verification process whereby the chamber pressure is altered to for a predicted relative body weight and while measuring or displaying the actual body weight. In some further examples, during the calibration procedures, if one or more measured pressure or ground reaction force values falls outside a safety range or limit, the particular measurement may be automatically repeated a certain number of times and/or a system error signal may be generated. The error signal may halt the calibration procedure, and may provide instructions to through the control panel 118 to perform certain safety checks before continuing.

Figure 2A:
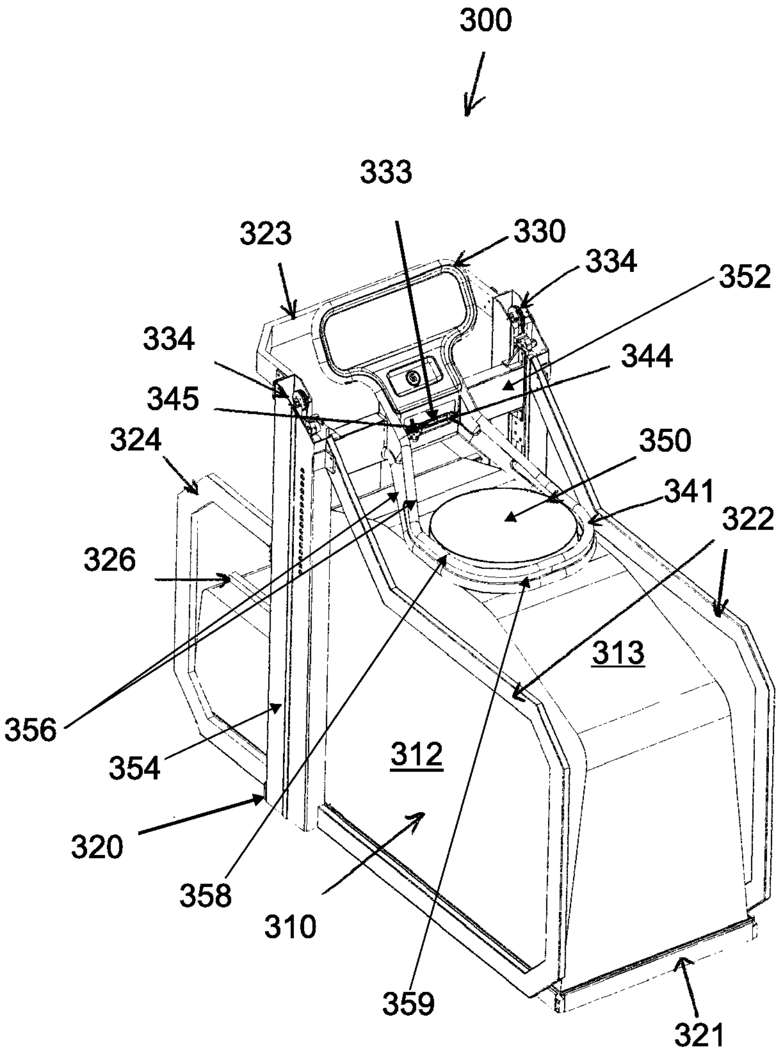
FIG. 2A is a perspective view of one example of a differential air pressure system.
Figure 2B:
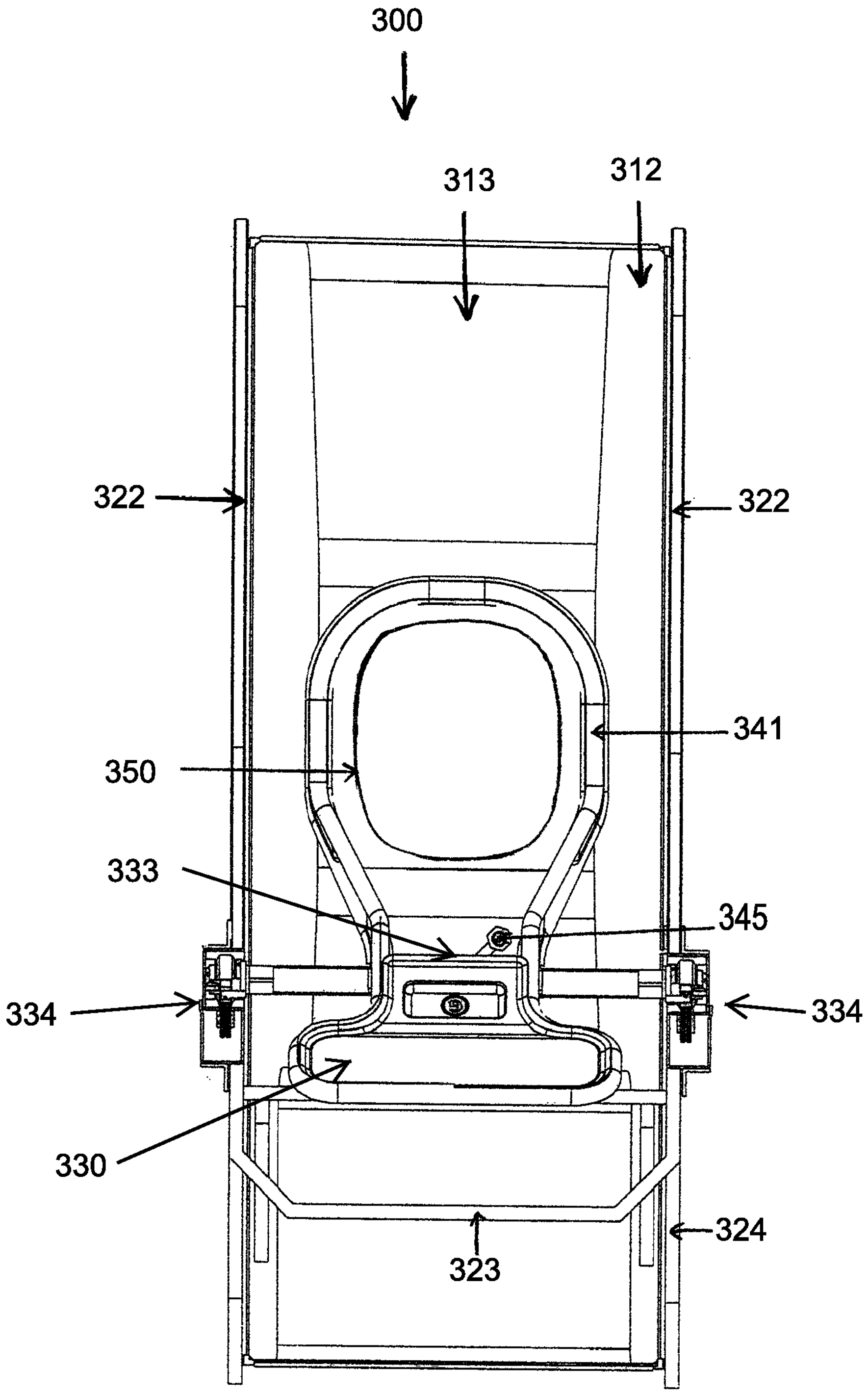
FIG. 2B is a top view of the system in FIG. 2A.
Figure 2C:
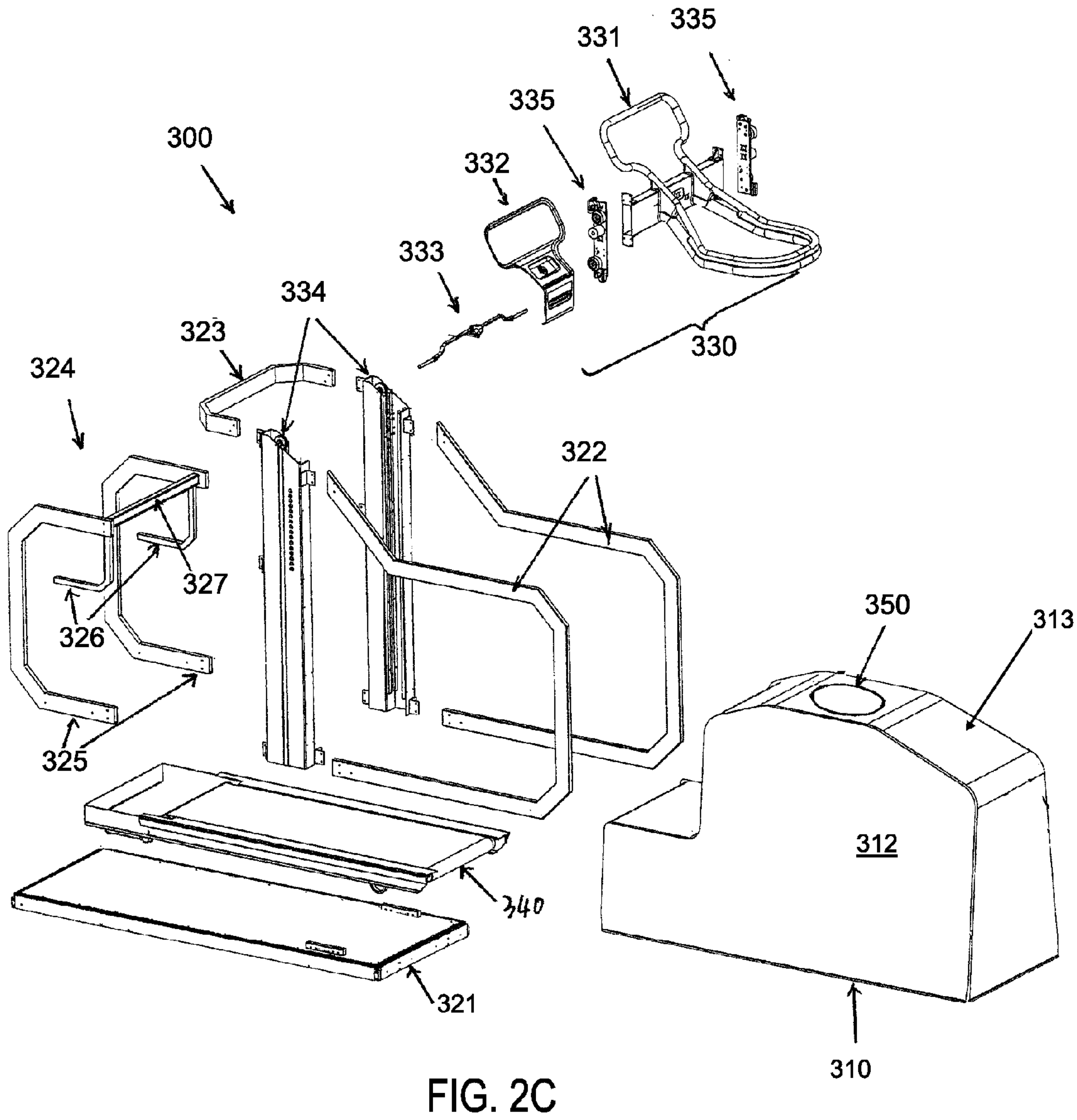
FIG. 2C is a perspective component view of the system in FIG. 2A.

Another example of a differential air pressure (DAP) system is illustrated in FIGS. 2A to 2C. This DAP system 300 comprises a pressure chamber 310 with a user seal 350, an exercise machine within the chamber 310 (not shown), a frame 320, and a console 330. The DAP system 300 may also comprise a height adjustment mechanism 334 to alter the height of a user seal 350, and a locking mechanism 333 may also be provided to maintain the adjustment mechanism 334 at a desired position. Features and variations of the DAP system 300 are discussed in greater detail below.

Pressure Chamber

Figure 5:
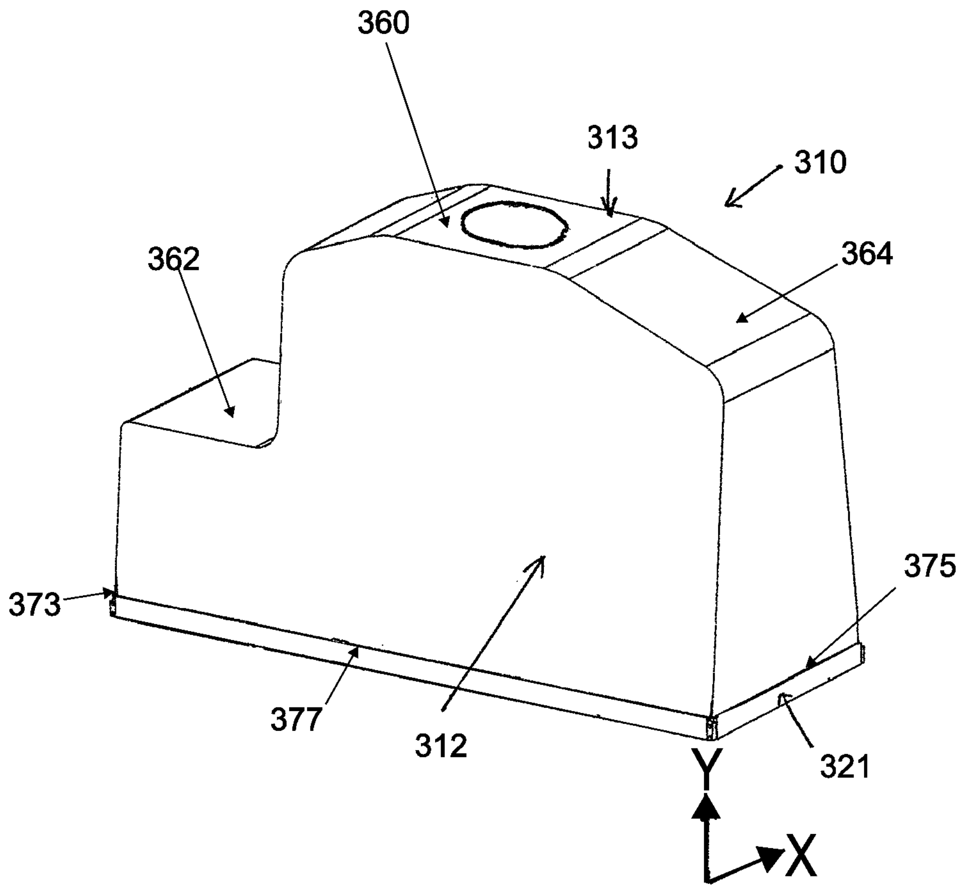
FIG. 5 is a perspective view of one embodiment of a pressure chamber attached to the base of a differential air pressure system.
Figure 11A:
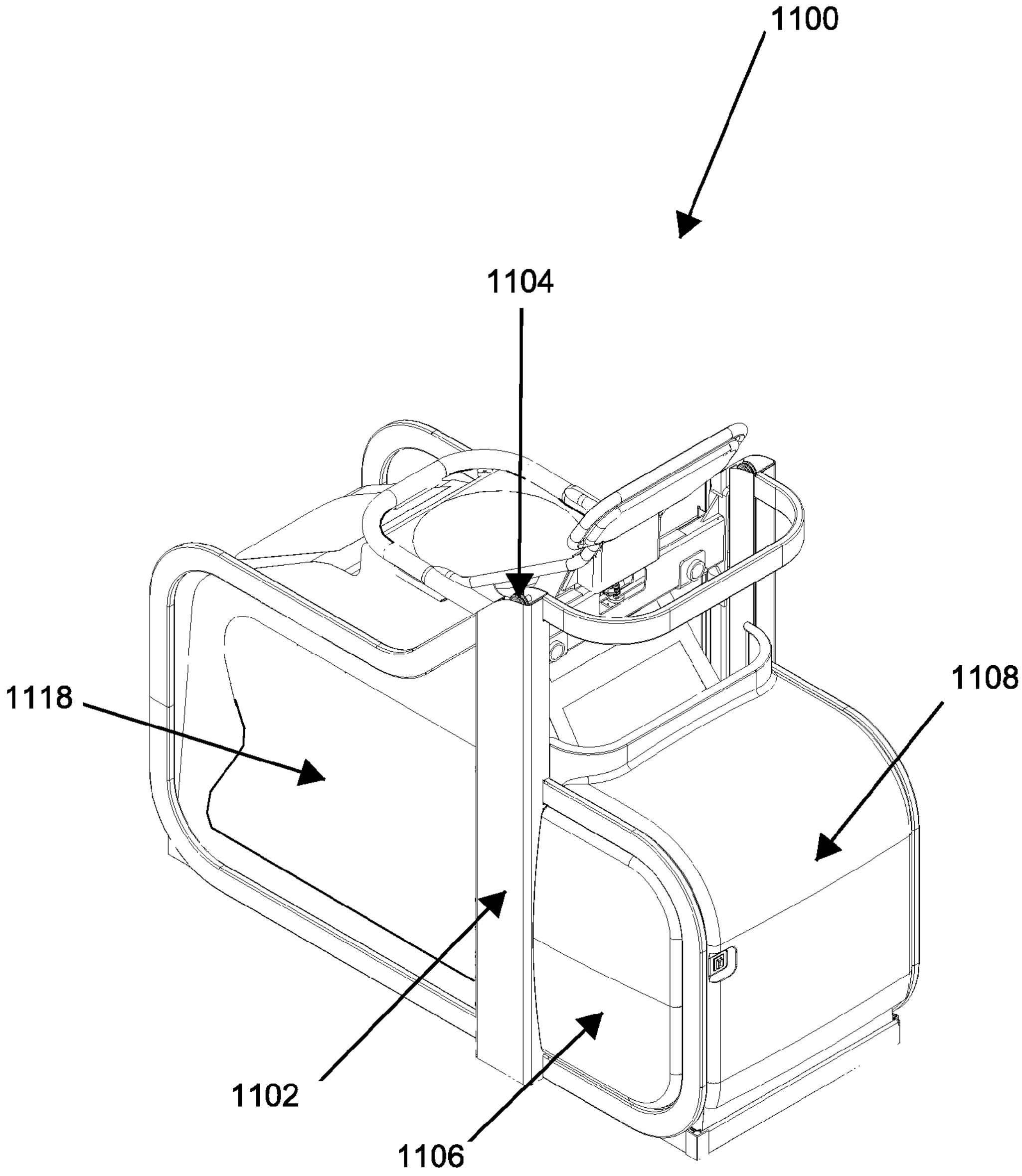
FIG. 11A is a perspective view of another example of a differential air pressure system.
Figure 11B:
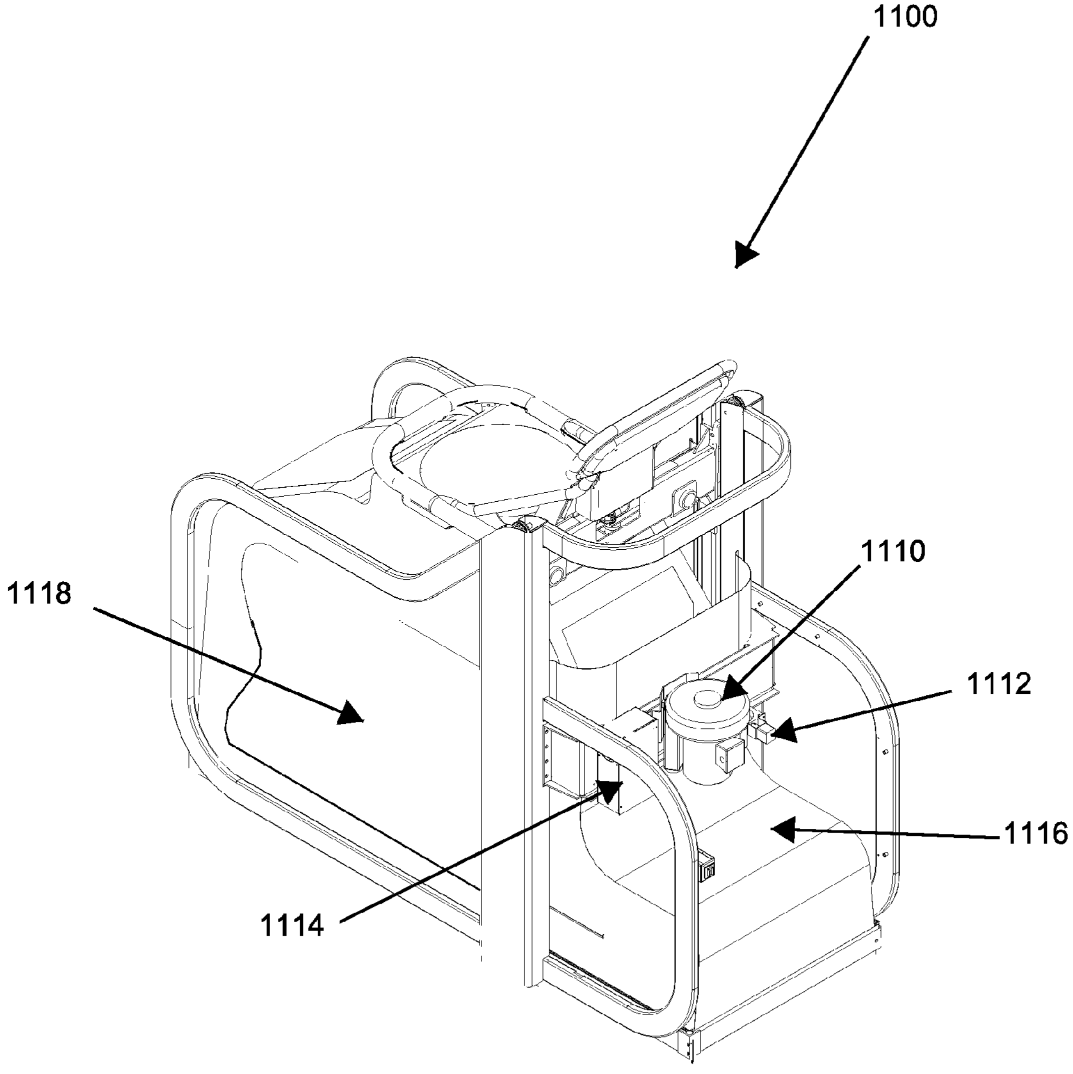
FIG. 11B is a perspective view of the system in FIG. 11A with its paneling removed.

FIGS. 2A and 2B schematically illustrate the DAP system 300 with the pressure chamber 310 in an expanded state. Although the chamber 310 is shown with surfaces having generally planar configurations, in use, at least some if not all of the surfaces may bulge outward when inflated or pressurized. The chamber 310 may be configured with a particular shape or contour when pressurized and/or depressurized or otherwise collapsed. Certain shapes or contours may be useful to accommodate particular movements or motions, including motion inside the chamber 310 and/or motion outside the chamber 310. Certain shapes or contours may also be useful in controlling the shape of the enclosure in the collapsed state to minimize loose fabric which would otherwise create a tripping hazard. In FIG. 2A, for example, the chamber 310 has a greater length relative to its width. The ratio between the length and the width of the chamber may be in the range of about 1.5:1 to about 5:1 or greater, in some examples about 2:1 to about 4:1 and in other examples in the range of about 2.5:1 to about 3.5:1. An elongate length may permit the use of a treadmill, and/or accommodate body movements associated with some training regimens. For example, an elongate chamber length may provide increased space for forward leg extensions and/or rearward leg kicks associated with running and other forms of ambulation. In other variations, the chamber may have a greater width than length, and the ratios of length to width may be the opposite of the ranges described above, or a shape or footprint different from a rectangle, including but not limited, to a square, circle, ellipse, teardrop, or polygon footprint, for example. Referring to FIG. 5, the chamber 310 may also have a variable width, with one or more sections of the chamber 310 having a different width than other sections of the chamber 310. For example, the chamber 310 may comprise a reduced superior central width 360, as compared to the superior anterior width 362 and/or the superior posterior width of the chamber 310. Also, the superior anterior width and the superior posterior width may be similar, while their ratios to the central superior width are about 5:3. In other examples, the ratio may in the range of about 1:2 to about 4:1 or higher, in some examples about 1:1 to about 3:1, and in other examples about 5:4 to about 2:1. The superior width of anterior, central and/or posterior regions may also be smaller or a greater than the inferior width 366, 368,370 of the same or different region. The ratio of a superior width to an inferior width may be in the range of about 1:4 to about 4:1, sometimes about 1:2 to about 1:2, and other times about 2:3 to about 1:1. The bag may be contoured to allow for volumetric efficiency in placing additional components in unused space. For example, as illustrated in FIG. 11B, a front section 1116 of the chamber 1118 may be brought downward and outward to allow room for placement of a blower 1110, valve 1112 and electronics 114 above the front section 116, for example. The contours and/or seams of the chamber may be rounded or curved using sufficient radii on corners to reduce fabric stresses, or may incorporate reinforcement patches where stresses are high.

Referring back to the DAP system 300 in FIGS. 2A to 2C, the superior to inferior widths of the anterior and posterior regions may be about 2:3, while the ratio in the central region may be about 2:5. One or more sections of the chamber 310 may comprise any of a variety of axial cross-sectional shapes, including but not limited to trapezoidal or triangular cross-sectional shapes. Other shapes include but are not limited to square, rectangular, oval, polygonal, circular, and semi-circular shapes (or other portion of a circle or other shape), and the like. Two or more sections of the chamber along the same directional axis may have the same or a different cross-sectional shape. A chamber 310 with a reduced superior central width (or other region adjacent to the user seal 350) may provide increased space above or outside the chamber 310 to accommodate arm swing during ambulation, permit closer positioning of safety handrails, and/or or use of ambulation aids (e.g. walker or cane). In other examples, the superior central width of the chamber, or other section of the chamber, may be increased relative to one or more other sections described above, and in some specific examples, the chamber may be configured to facilitate resting of the arms or hands on the chamber, or even direct gripping of the chamber with one or more handles.

The chamber of a DAP system may have a fixed or variable height along its length and/or width, as well as a variable configuration along its superior surface. The vertical height of the chamber may be expressed as a percent height relative to a peak height or to a particular structure, such as the user seal. The peak height of a chamber may be located anywhere from the anterior region to the posterior region, as well as anywhere from left to right, and may also comprise more than one peak height and/or include lesser peaks which are shorter than the peak height but have downsloping regions in opposite directions from the lesser peak. The superior surface may comprise one or more sections having a generally horizontal orientation and/or one or more sections with an angled orientation that slopes upward or downward from anterior to posterior, left to right (or vice versa). Some configurations may also comprise generally vertically oriented sections (or acutely upsloping or downsloping sections) that may separate two superior sections of the chamber. As depicted in FIG. 2C, the chamber 310 may comprise an anterior region with a height that is about 50% or less than the height of the user seal 350, but in some variations, the height may be anywhere in the range of about 1% to about 100% of the peak height, sometimes about 5% to about 80%, and other times about 20% to about 50%. A reduced height region may provide additional space within the chamber for internal structures, such a treadmill, while providing space above the reduced height region for external structures. The internal and external structures may have a fixed location or a movable position.

Figure 3A:
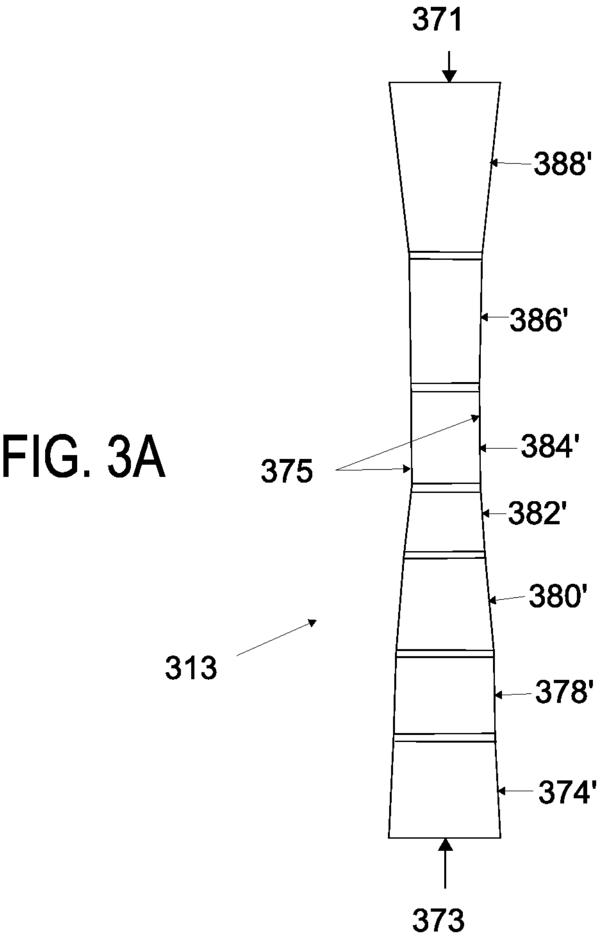
FIGS. 3A and 3B are schematic illustrations of a middle panel and a side panel of one example of a pressure chamber, respectively.
Figure 3B:
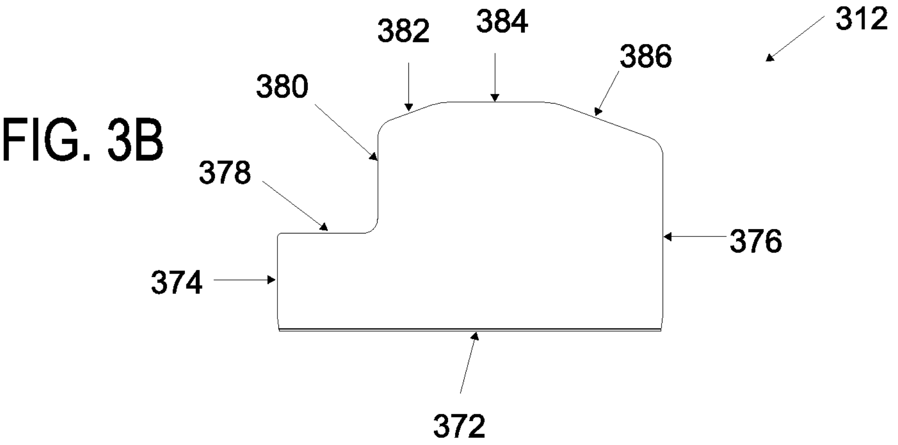
Figure 6A:
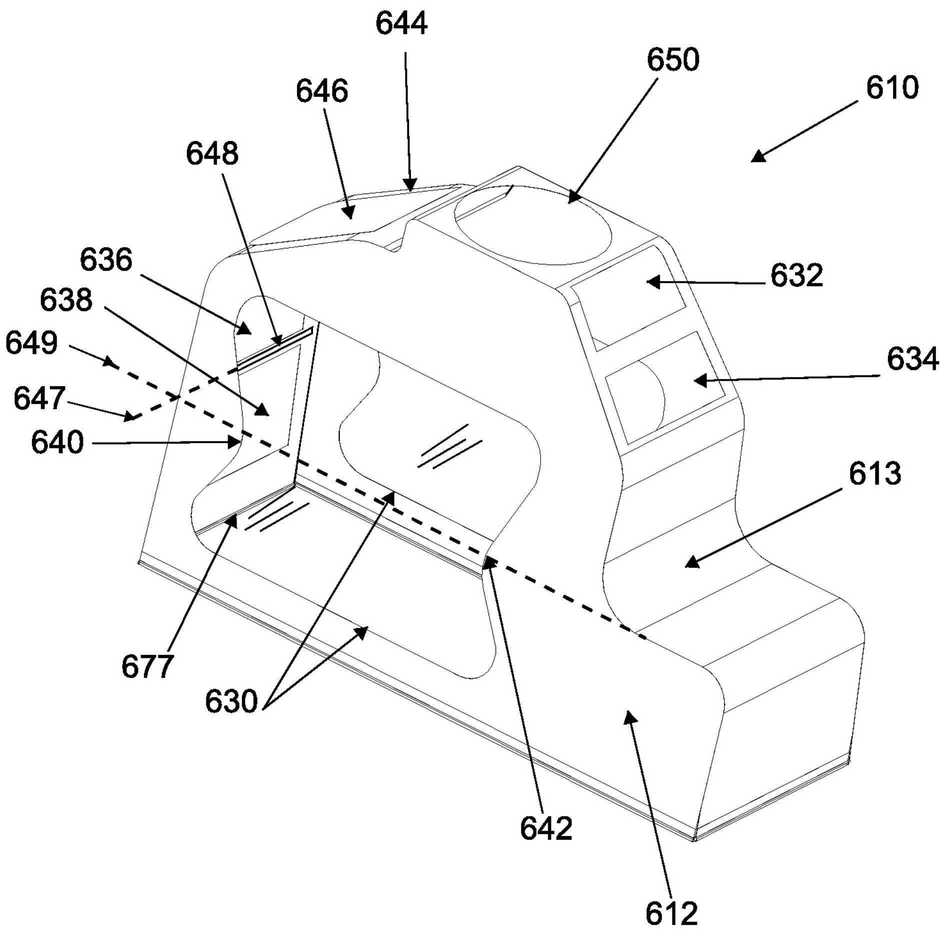
FIGS. 6A and 6B are schematic anterior and posterior perspective views, respectively of another embodiment of a pressure chamber in an expanded state.
Figure 6B:
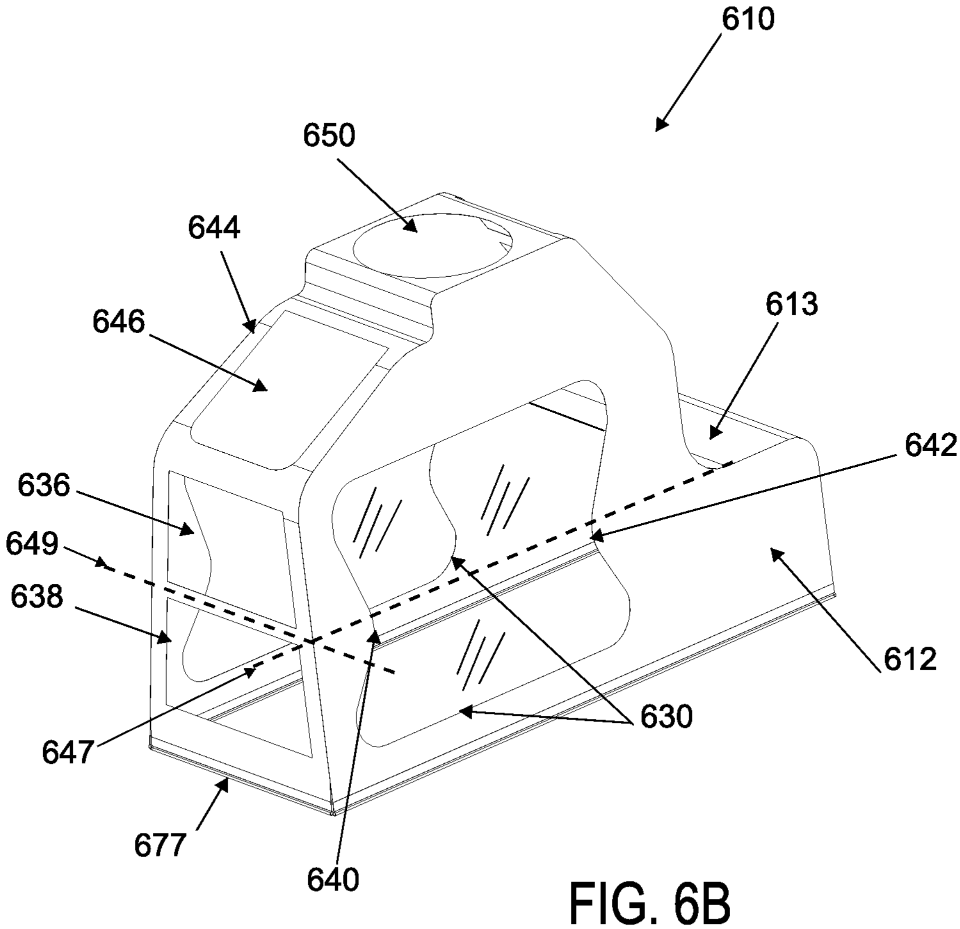

The pressure chamber may be assembled or formed by any of a variety of manufacturing processes, such as shaping and heating setting the enclosure, or attaching a plurality of panels in a particular configuration. The chamber 310 illustrated in FIGS. 2A to 2C comprises two side panels 312 and a middle panel 313, but in other variations, fewer or greater number of panels may be used to form the same or a different chamber configuration. For example, a side panel may be integrally formed with one or more portions of the middle panel or even the other side panel. As schematically illustrated in FIGS. 3A and 3B, these panels 312 and 313 may be cut or manufactured from sheet-like material but are then attached in non-planar configurations. The middle panel 313 of the chamber 310 may comprise an elongate sheet of material having an anterior edge 371, a posterior edge 373 and two non-linear, centrally narrowed lateral edges 375, such that the middle panel 313 has a greater width anteriorly and posteriorly than centrally. The side panels 312 may have an irregular polygonal shape, comprising a generally linear horizontal inferior edge 372, a generally linear vertical anterior edge 374, and a generally linear vertical posterior edge 376, while the superior edge comprises an generally horizontal first superior edge 378, a generally vertical second superior edge 380, a generally upsloping third superior edge 382, a generally horizontal fourth superior edge 384, and a generally downsloping fifth superior edge 386. The transition from one edge to the adjacent may be abrupt or gradual, and may be angled or curved. Although the side panels 312 and the lateral edges 375 of the middle panel 313 may be generally symmetrical or minor images, while in other variations the side panels and/or the lateral edges of the middle panel may have asymmetric configurations. The characterization of some or all the edges of the shape into general orthogonal orientations (e.g. anterior/posterior/superior/inferior) is not required may vary depending upon the reference point used. Thus, in the example above, the second superior edge 380 may also be characterized as an anterior edge, while edge 378 may be characterized as either an anterior or superior edge. In other variations, one or more of the edges of the panel may be generally curved or non-linear, and may be generally upsloping, downsloping, vertical, or horizontal, and may comprise multiple segments. The panels may have a shape the promotes folding such as a stiffer outer section and more flexible inner section as shown in FIGS. 6A and 6B, which resembles a butterfly or hourglass shape, but could also be any of a variety of other suitable shapes with a reduced central dimension.

Figure 4A:
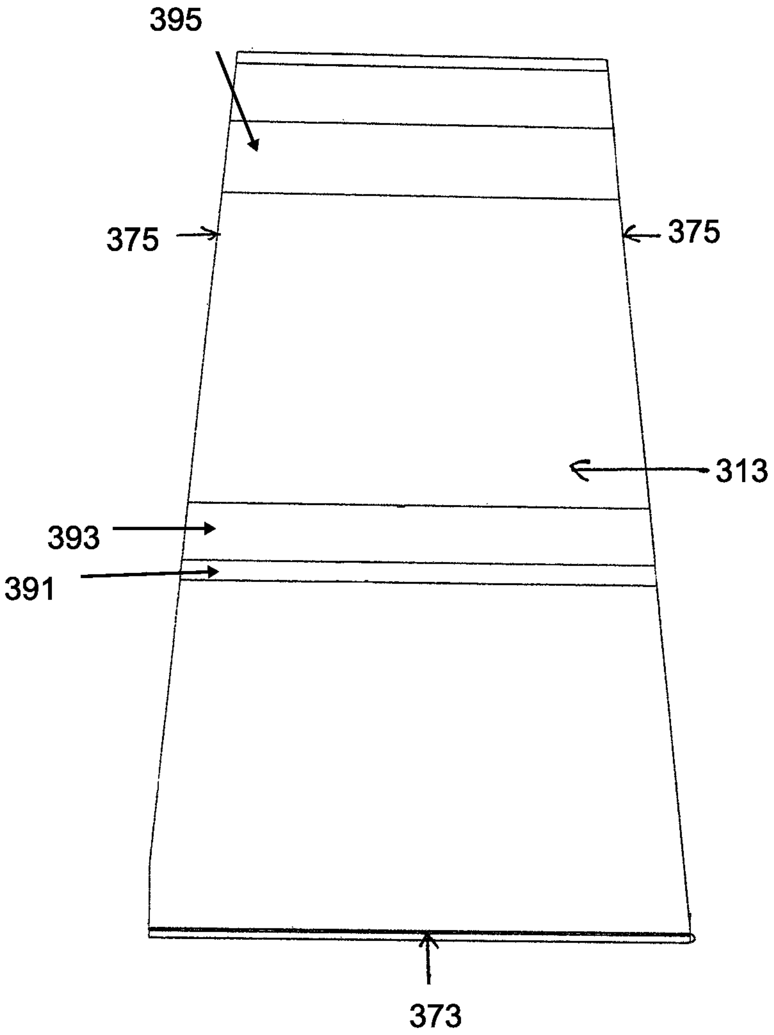
FIGS. 4A and 4B illustrate one embodiment of a pressure chamber.
Figure 4B:
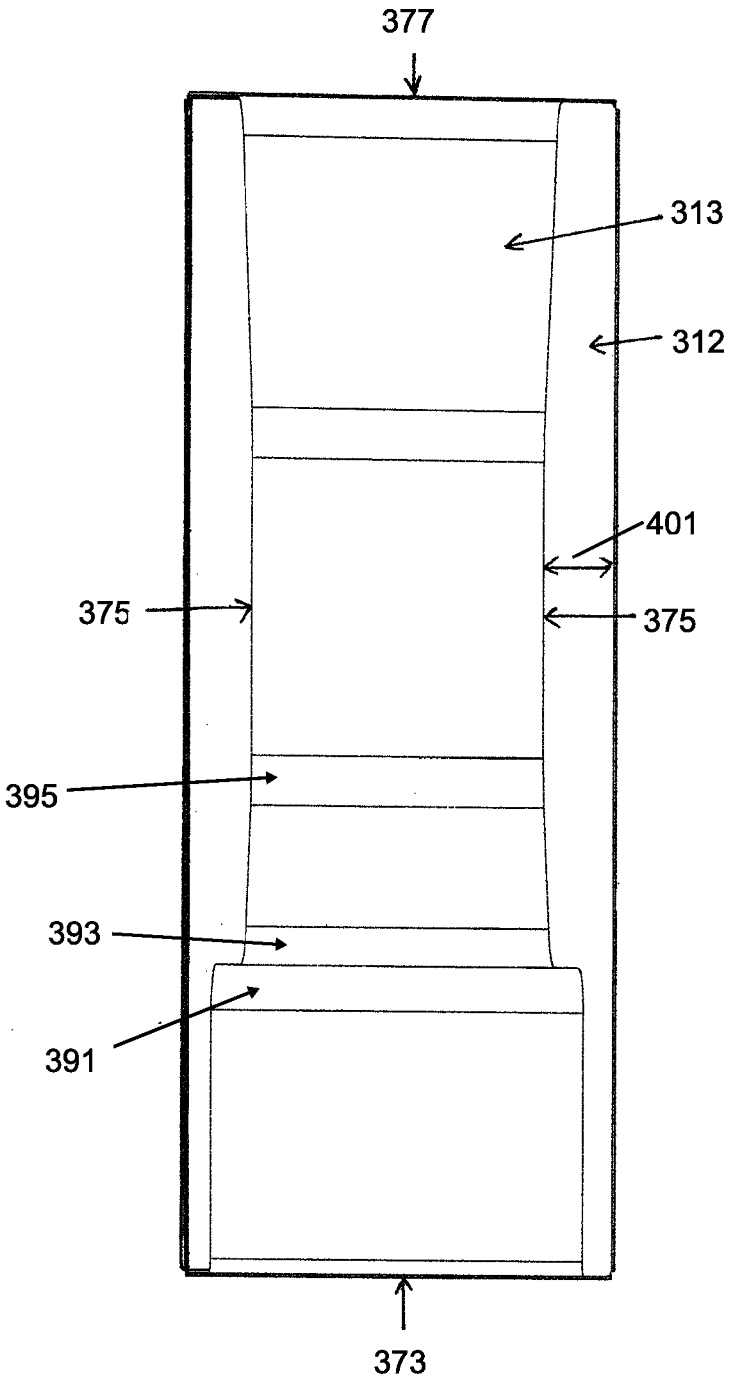

The edges or edge regions of the two side panels 312 may be attached to the lateral edges 375 (or lateral edge regions) of the middle panel 313, e.g. the anterior edge 374 of the side panel 312 is attached to first edge 374' of the middle panel 313, etc. The various edges of the middle panel 313 may be characterized (from anterior to posterior, or other reference point) as parallel edges 378' and 384', tapered edges 374', 380' and 382' or flared edges 388'. The edge or edge regions may be attached and/or sealed by any of a variety of mechanisms, including but not limited to stitching, gluing, heat melding and combinations thereof. The chamber may also be formed from a single panel which may be folded or configured and attached to itself (e.g. edge-to-edge, edge-to-surface or surface-to-surface) to form a portion or all of the chamber. FIGS. 4A and 4B are orthogonal frontal view superior views, respectively of the chamber 310 in an assembled and expanded state, and schematically depicting the contours of the chamber 310. FIG. 4A schematically illustrates the wider base and narrower superior surface of the chamber 310, which may provide an offset or a gap 401 between side panel 312 of the chamber 310, as depicted in FIG. 4B. In some examples, a superiorly tapered chamber may reduce the amount of fabric or material used and/or may reduce the degree of bulge when the chamber is pressurized.

In some embodiments, the chamber or panels of the chamber may be configured with pre-determined fold lines or folding regions that may facilitate folding or deflation of the chamber along to a pre-determined shape. For example, the chamber may have an accordion or bellows-like configuration that biases the chamber to collapse to a pre-determined configuration along folds with an alternating inward and outward orientation. The pre-determined fold lines include but are not limited to the interface between flexible and rigid regions of the chamber, creases along a panel, or panel regions between generally angled edges of adjacent panels, for example. In some variations, fold lines may be creases or pleats provided by heat setting or mechanical compression. In other variations, fold lines may be made by a scoring or otherwise providing lines or regions with reduced thicknesses. Fold lines may also be provided along a thickened region, rigid region, ridge or other type of protrusion. Other fold lines may be provided by stitching or adhering strips of the same or different panel material to the chamber, and in other variations, stitching or application of curable or hardenable material (e.g. adhesive) alone may suffice to control folding. In still other variations, fold lines may be provided by attaching or embedding one or more elongate members (e.g., a rail or a tread made by NITINOL™) along the chamber. An elongate member may have any of a variety of characteristics, and may be linear or non-linear, malleable, elastic, rigid, semi-rigid or flexible, for example. The chamber or panels may comprise pre-formed grooves or recesses to facilitate insertion and/or removal of the elongate members, and in some variations, may permit reconfiguration chamber for different types of uses or users. In some embodiments, the fold-lines may comprise one or more mechanical hinge mechanisms between two panels (e.g., living hinges) that are either attached to the surface of the chamber or inserted into chamber pockets. Each fold line of a chamber may have the same or a different type of folding mechanism. Collapse of the chamber in a pre-determined fashion may also be affected by elastic tension elements or bands attached to the chamber.

As illustrated in FIGS. 4A and 4B, the middle panel 313 of the chamber 310 may comprise one or more fold lines 391, 393 and 395 which may help the chamber deflate or collapse into a pre-determined shape or configuration. In some examples, the pre-determined shape may facilitate entry and/or separation between the user and the system by reducing protruding folds or surface irregularities that may trip or otherwise hinder the user. The fold line 393 may be configured (e.g. with an internal angle greater than about 180 degrees by virtue of the side panel shape) to fold the adjacent external surfaces of the middle panel 313 against each other. This configuration in turn, may facilitate the nearest fold lines 391 and 395 to fold so that their adjacent internal surfaces fold against each other. The pre-determined fold lines 391, 393 and 395 in the anterior region of the chamber may result in a corresponding flattening of the posterior chamber.

As illustrated in FIG. 5, the front and back edges 373 and 375 of the middle panel 313 and the inferior edge 372 of the side panels are attached to the system platform or base 321 rather than a flexible panel or material, but in other variations, an inferior panel may be provided. The side panels 312 may be made from the same or different material as the middle panel 313 of the chamber 310, and in some variations, the side panels may also comprise different materials. In some variations, the stretch or flexible properties (or any other material properties) may be anisotropic. For example, the middle panel 313 of the chamber 310 may be made from a less stretchable material in order to limit the chamber's expansion in transverse direction (i.e., along X axis in FIG. 5). The side panels 312 may be made from a more stretchable material, which may or may not redistribute the tension acting on the less stretchable portions of the chamber 310. The side panels 312 may comprise a relatively more flexible material, which may facilitate a pre-determined folding pattern of the middle panel 313 when deflated or collapsed. The chamber 310 may be made of any suitable flexible material, e.g., a fabric (woven or nonwoven), a polymeric sheet (e.g., polyurethane, polypropylene, polyvinylchloride, Nylon®, Mylar®, etc.), leather (natural or synthetic), and the like. The materials may be opaque, translucent or transparent. In some embodiments, the outer surface of the middle panel 313 may be coated with anti-slip materials or coatings, and/or may comprise ridges or other surface texturing to resist slipping when a user steps onto the deflated chamber 310.

Figure 6C:
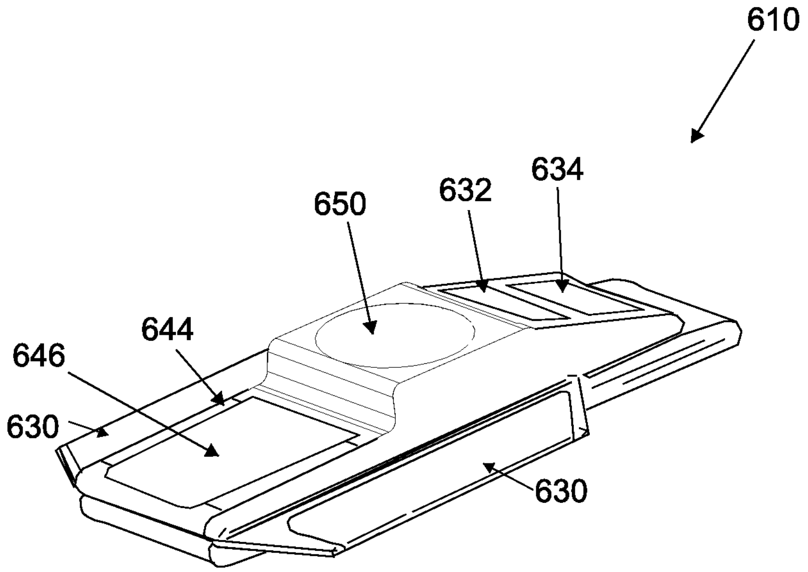
FIG. 6C is a schematic anterior perspective view of the pressure chamber in a collapsed state.

FIGS. 6A to 6C depict one example of a pressure chamber 610 comprising multiple panels with different material characteristics. Here, the side panels 612 and the middle panel 613 further comprise generally airtight transparent windows 630, 632, 634, 636 and 638. The user seal 650 may also comprise one or transparent or translucent regions. In some examples, transparent materials may permit a healthcare provider or other observer to view the movement of the user (e.g. gait analysis), or to improve the safety of the system by permitting viewing of the chamber contents, in the expanded and/or collapsed states. The windows may also permit the user to view his or her lower limbs, which may promote gait stability and/or balance. The side windows 630 of the side panels 612 may also comprise non-linear, concave edges 640 and 642 anteriorly and posteriorly. In some examples, the concave edges 640 and 642 may facilitate folding of the side panels 612 along fold line 647. As shown in FIG. 6C, the outfolding, rather than infolding, of the side windows 630 may also be facilitated by the bulging side windows 630 in the pre-collapsed/pressurized state. In some examples, by promoting the outfolding of the side windows 630 in the collapsed configuration, there may be less chamber material adjacent to the user seal 650 which a user may trip or step on when entering the system. This may permit the superior posterior section 644 of the lie in a flatter orientation and to span the area from the posterior edge 677 of the middle panel 613 to the user seal 650. In some variations, a rod or other elongate element 648 (as shown in FIG. 6B) may be attached horizontally between the posterior windows 636 and 638 to facilitate the folding along fold line 649. The elongate element 548 may be attached to the interior or exterior surface, and/or partially or completely embedded within the panel material itself. In some examples, the rod or elongate element may comprise a significant weight such that upon depressurization of the chamber, the weight of the rod and its location along a sloped surface of the chamber may facilitate the inward folding of the chamber. A non-slip layer 646 of material may be provided on the superior posterior section 644, which may promote safe ingress and egress from the chamber 610. A non-slip layer may also be reinforced or made of substantially stiff material to assist in contouring of the chamber to aid in folding and prevent wrinkling where deflated, thereby reducing the trip hazard. In other examples, the concave or inwardly angled edges may be located more inferiorly or more superiorly, and may also be located along other edges of the window (or panel) or multiple sites may be found along one edge. In still other variations, one or more edge may comprise a convex or outwardly angled edge, which may facilitate folding in the opposite direction.

A DAP system may comprise an attachment mechanism to couple and/or seal a pressure chamber to the base of the system in a sufficiently airtight manner to maintain pressurization within the chamber. One example of an attachment mechanism is illustrated in FIGS. 7A to 7D. The inferior edges of the side panels 768 and posterior inferior edge of the middle panel 770 may comprise one or more sealing structures that engage and seal along a corresponding recess or groove along the base 700. The sealing structure may comprise any of a variety of structures or combinations of structures having a transverse dimension that is greater than the opening or slot 762 along the recess or groove 760, including but not limited to inverted T-structures, flanges and the like. Alternatively, the chamber may also be attached to the base using welding, adhesives, hook-and-loop fasteners or other suitable attachment methods known to the ordinary skilled in the art.

Figure 7A:
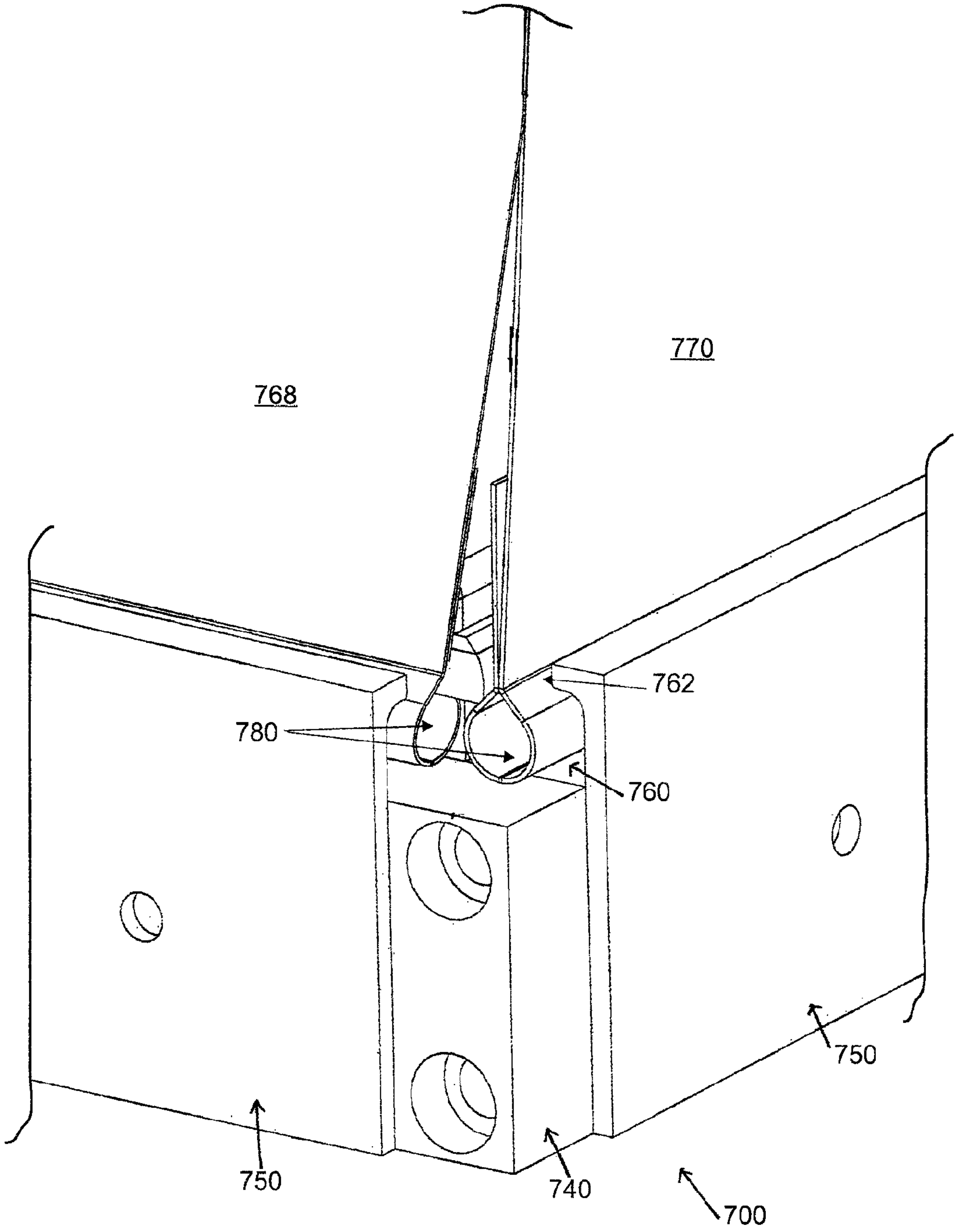
FIG. 7A is a perspective view of one embodiment of an attachment interface between an pressure chamber and the base of a differential air pressure system.
Figure 7B:
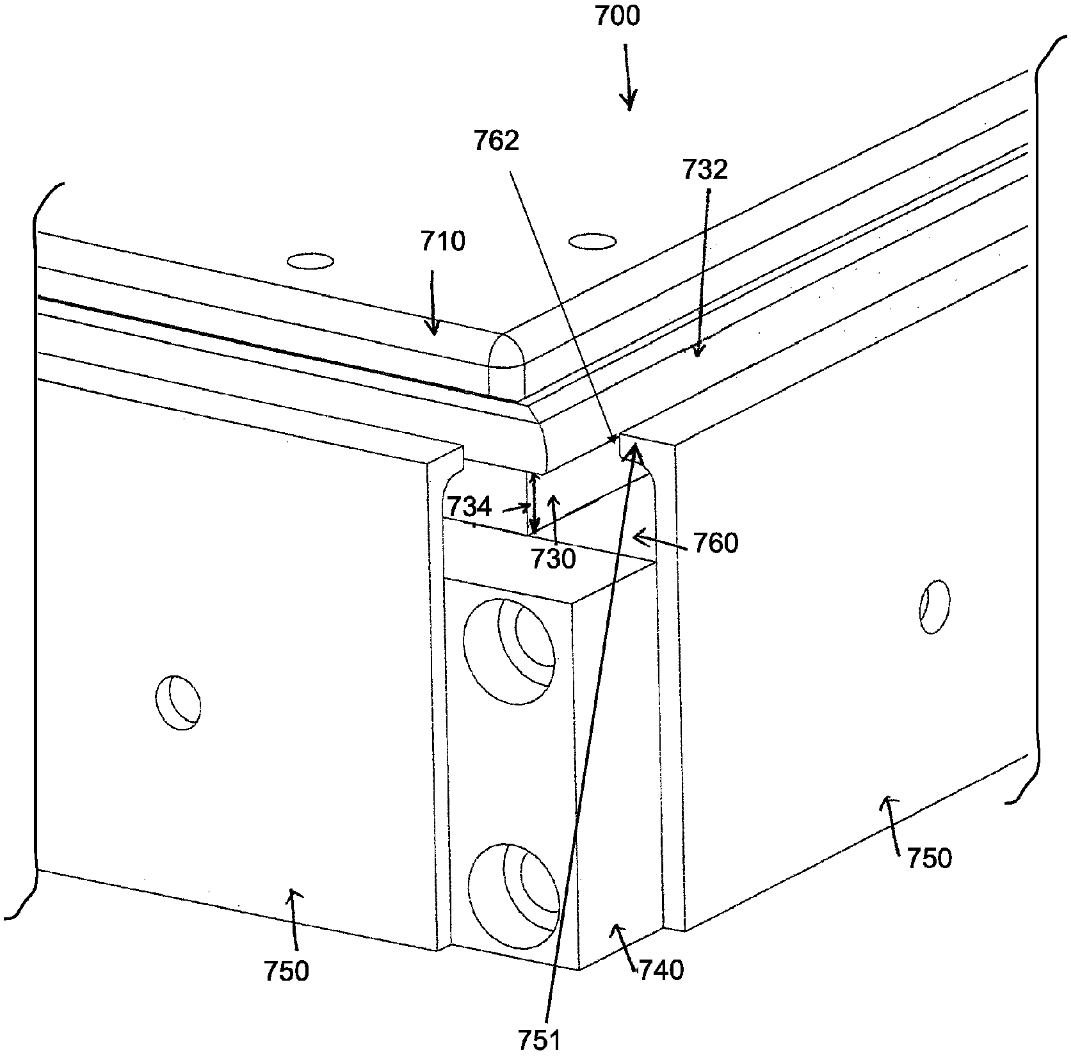
FIG. 7B is a detailed view of the attachment interface from FIG. 7A without the pressure chamber.
Figure 7C:
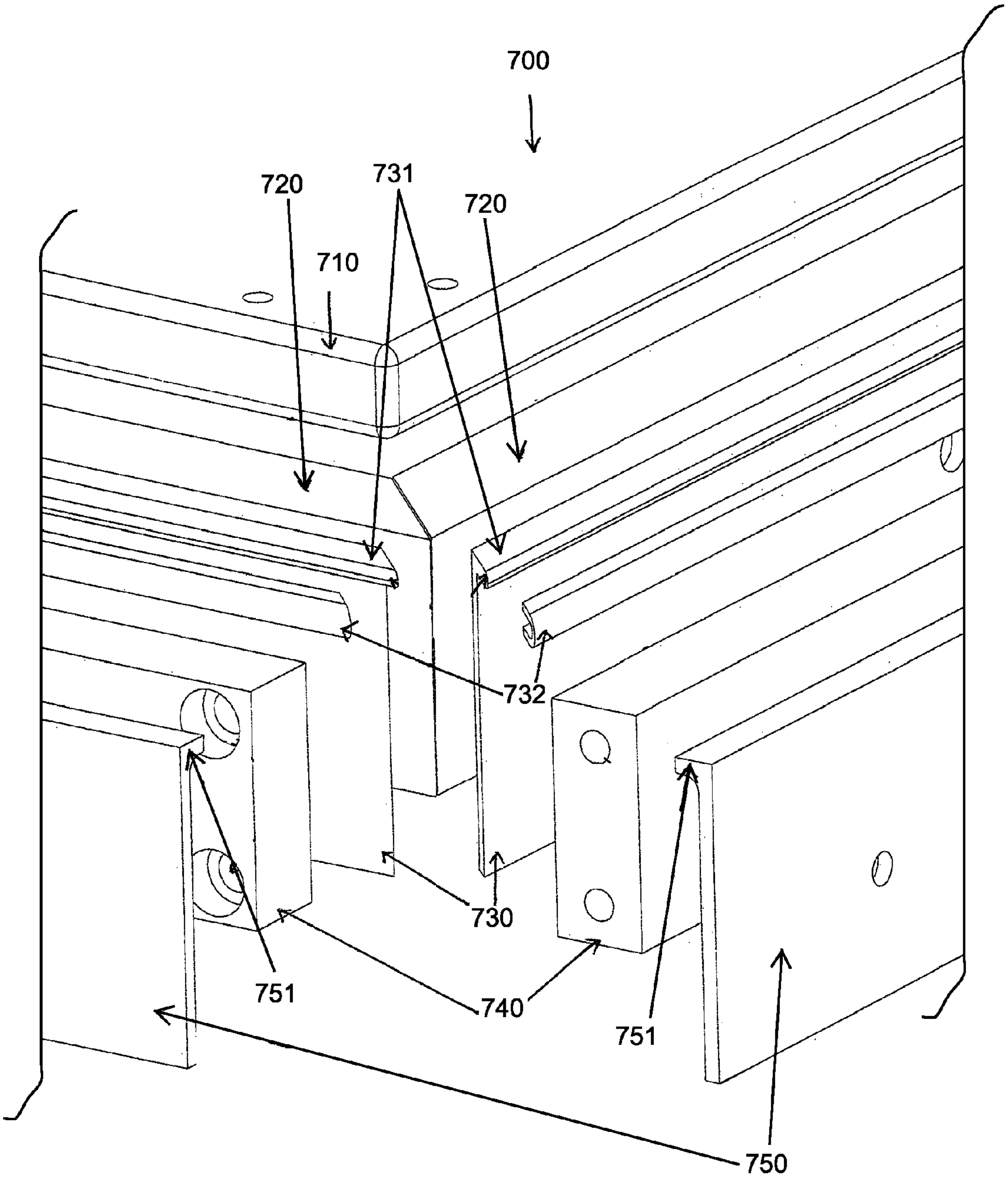
FIG. 7C is a component view of the base of the differential air pressure system of FIG. 7A.
Figure 7D:
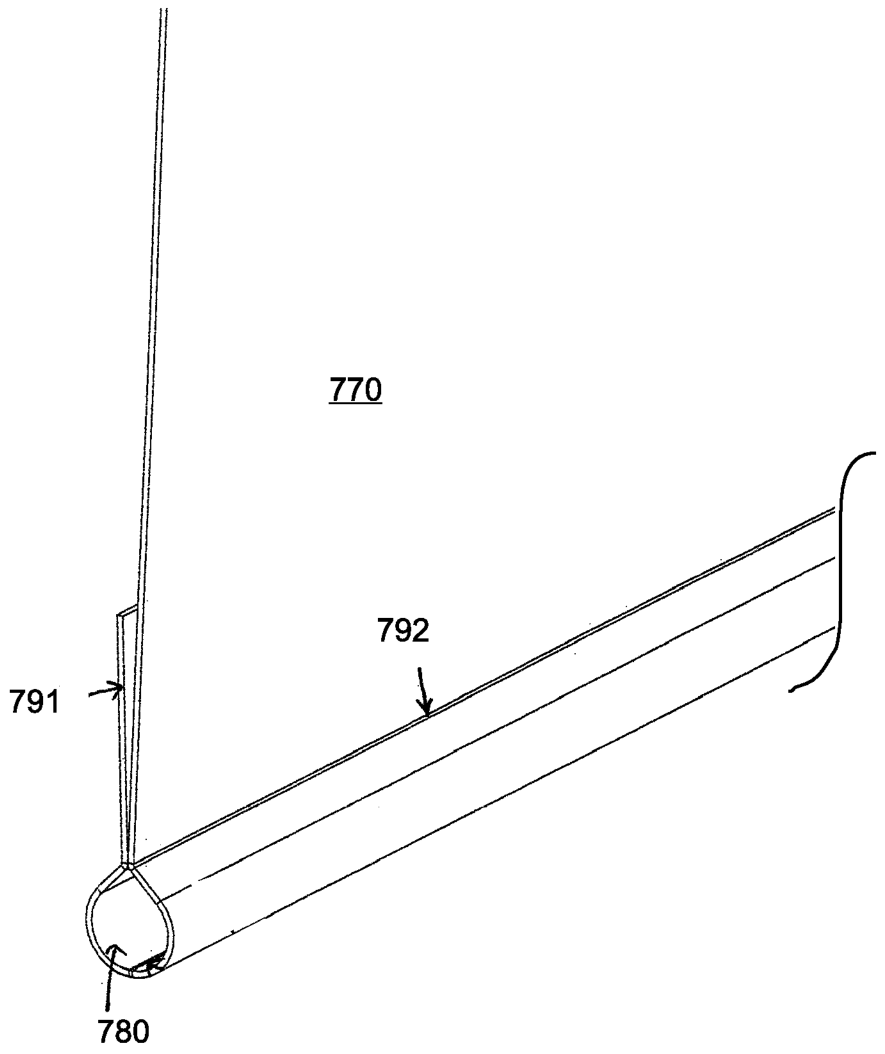
FIG. 7D is a detailed view of the bottom edge of the chamber of FIG. 7A.

As depicted in FIG. 7D, the sealing structure may comprise a tubular structure 780 formed by folding and adhering or attaching the panel 770 back against itself. In other variations, the tubular structure may be formed by any of a variety of processes, including but not limited to extrusion and the like. The panel 770 may be folded inwardly (as depicted in FIG. 7D) or outwardly (as depicted in the alternate embodiment FIG. 14), or may comprise tabs which may fold in different directions. The sealing structure may comprise the same or different material (or reinforcement structure, if any) as the rest of the panel 770, and may or may not have a different thickness.

The tubular structure 780 may be seated in the groove 760 such that the transverse width of the tubular structure 780 resists pullout from the groove 760. In some examples, a reinforcement member, such a rod or other elongate member, may be inserted into the tubular structure 780 to further resist pullout, while in other variations, the rigidity of the panel material in a tubular configuration alone may be sufficient. In still other configurations, the inferior edges of the panel material may be attached or integrally formed with a flange or other structure to resist pullout. In other examples, a specific sealing structure is not required along edge of the panels and instead, the base may comprise a clamping structure which may provide a friction interface to retain and seal the panels.

In the particular embodiment of FIGS. 7A to 7C, the system base 700 may comprise a deck 710 with inner retaining frame 730 and an outer retaining frame 750 configured to attach to the sealing structures of the chamber panels 768 and 770. Specifically, the inner and outer retaining frame 730 and 750 together form an elongate recess or groove 760 with a slot 762. The inner and/or outer retaining frames 730 and 750 may comprise a flange or transverse projection 731 and 751, respectively, to resist pull out. In some examples one or both flanges 731 and 751 include a gasket 732 to augment the sealing characteristics of the frames 730 and 750. The gasket 732 may comprise any of a variety of suitable materials (e.g., rubber, plastic polymer, etc.). To position the tubular structure 780 (or other sealing structure of the chamber panels) within the groove 760, one or more portions of the outer retaining frame 750 may be removed or at least separated from the inner retaining frame 730 to permit placement of the tubular structure 780. The outer retaining frame 750 may then be reattached or tightened to the inner frame 730. Any of a variety of clamps or fasteners (e.g. bolts or screws) may be used to attach the frames 730 and 750. In some examples, the inner and outer frame may be integrally formed, such that the tubular structure 780 may be inserted into the frame by passing or sliding one end of the tubular structure 780 into one end of the groove 760 until the tubular structure 780 is seated. In other examples, the sealing structure may have a tapered cross-sectional shape that may be directly inserted into the slot and locks to the groove when fully inserted. In other examples, the outer retaining frame 750 may comprise a hinge or other which may be displaced or pulled away to facilitate access. The hinge may be unbiased in any particular configuration, or may be spring-loaded to maintain either a closed or open position, and may further comprise a locking mechanism to maintain the hinge in the closed position to retain the sealing structure.

Figure 14:
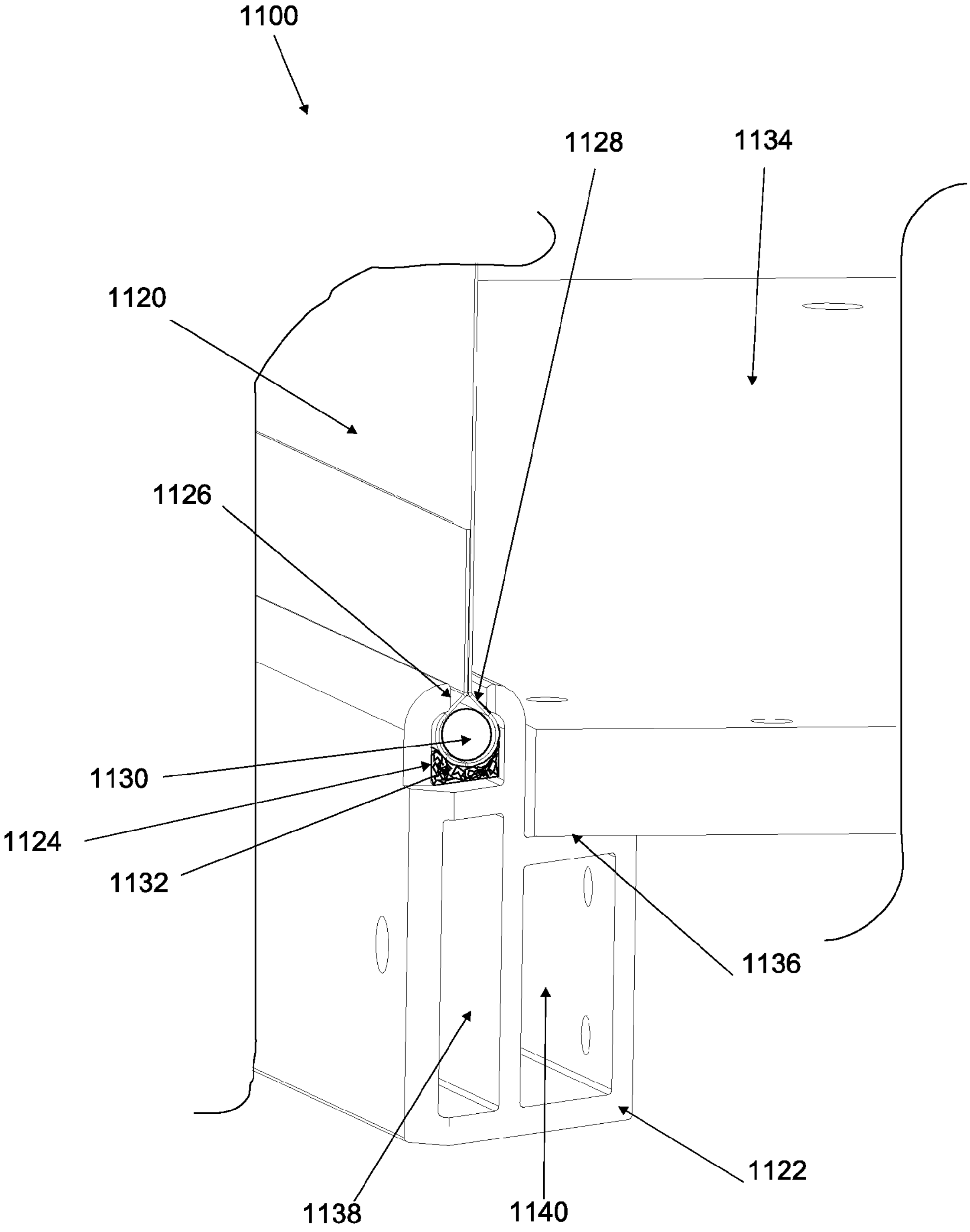
FIG. 14 is a schematic perspective view of the rear retaining rail, posterior chamber panel, and platform of the system in FIG. 11A.

The deck 710 may have separate deck support 720, but in other variations the inner retaining frame may be further configured to support the deck 710. The frame assembly comprising the inner and outer retaining frame 730 and 750 may further comprise with frame reinforcement bars 740, which may dampen vibration or torsion of the frames 730 and 750. In the example depicted in FIG. 7C, the reinforcement bars 740 are located between the inner and outer retaining frames 730 and 750, but in other variations may be located internal to the inner frame and/or external to the outer frame. In other variations, the reinforcement bars may be joined to each other using any of a variety of fasteners or attachment structures, or may be integrally formed into a single reinforcement structure, such as an extrusion, and may also be integrally formed with the inner and/or outer retaining frame. The deck 710 comprise a rectangular configuration or any other shape, such as a triangle, square, circle, ellipse, polygon or combination thereof, as can the deck support, inner retaining frame, reinforcement bar and outer retaining frame. FIG. 14 schematically depicts another example of a DAP system 1100 where the attachment of the chamber panel 1120 with an extruded, unibody retaining frame member 1122. The unibody retaining frame member 1122 comprises a groove 1124 configured with a slot 1126 configured to retain a tubular fold 1128 of the panel 1120. To further augment the attachment and/or sealing of the panel to the frame member 1122, one or more rods 1130 (or other elongate structures) are placed within the tubular fold 1128 to resist pullout of the panel 1120 by mechanical interference with the groove 1124 and slot 1126. A foam member 1132 may also be positioned in the groove 1124. The foam member 1132 may be open-celled or closed-cell, and may have a pre-cut shape or may be injected in a flowable form into the groove 1124. The foam member 1132 may or may not adhere to the tubular fold 1128 and/or the surface of the groove 1124. In variations where the foam is adhesive, the foam membrane may comprise a polymer with adhesive properties, or the foam, groove and/or fold may be coated with an adhesive. The foam properties may vary, and in some variations, may comprise a compressible, elastic foam which may push the tubular fold 1128 and/or rod 1130 up against the slot 1126, to further augment the sealing of the panel 1120 and frame member 1122. The foam may be inserted into the groove 1124 at the point-of-manufacture or during assembly at the point-of-use. In some variations, the rod 1130 is inserted after the foam member 1132 and the tubular fold 1128 are positioned in the groove 1124. The foam member 1132 is compressed as the rod is inserted, thereby increasing the active sealing of the chamber to the base.

As further depicted in FIG. 14, the frame member 1122 may also be configured to support the deck 1134 of the DAP system 1100. Here, the frame member 1122 comprises an interior ledge structure1136 to support the deck 1134. As also depicted in FIG. 14, the frame member 1122 may comprise a hollow configuration with one or more extruded cavities 1138 and 1140, which may reduce the weight and cost of the frame member. In other examples, the unibody frame member may have a solid configuration.

As mentioned previously, in some variations, a rod or other retention structure may be slid or otherwise placed within the tubular structure 780. The retention structure may have any of a variety of axial cross-sectional shapes. In some examples, the retention structure may have a teardrop shape or other complementary shape to the groove 760 and opening 762 of the retaining frames 730 and 750. In still other variations, a curable material may be injected into the tubular structure and hardened to resist separation and may also further seal the chamber to the base. The retention structure may also comprise a flexible cable that may be cinched or tightened around the inner retaining frame. When the chamber is deflated, due to both gravity and/or the weight of the chamber panels and/or the height adjustment mechanism, the tubular structures may separate from the slot and accelerate air leakage out of the chamber.

Height Adjustment System

Figure 13:
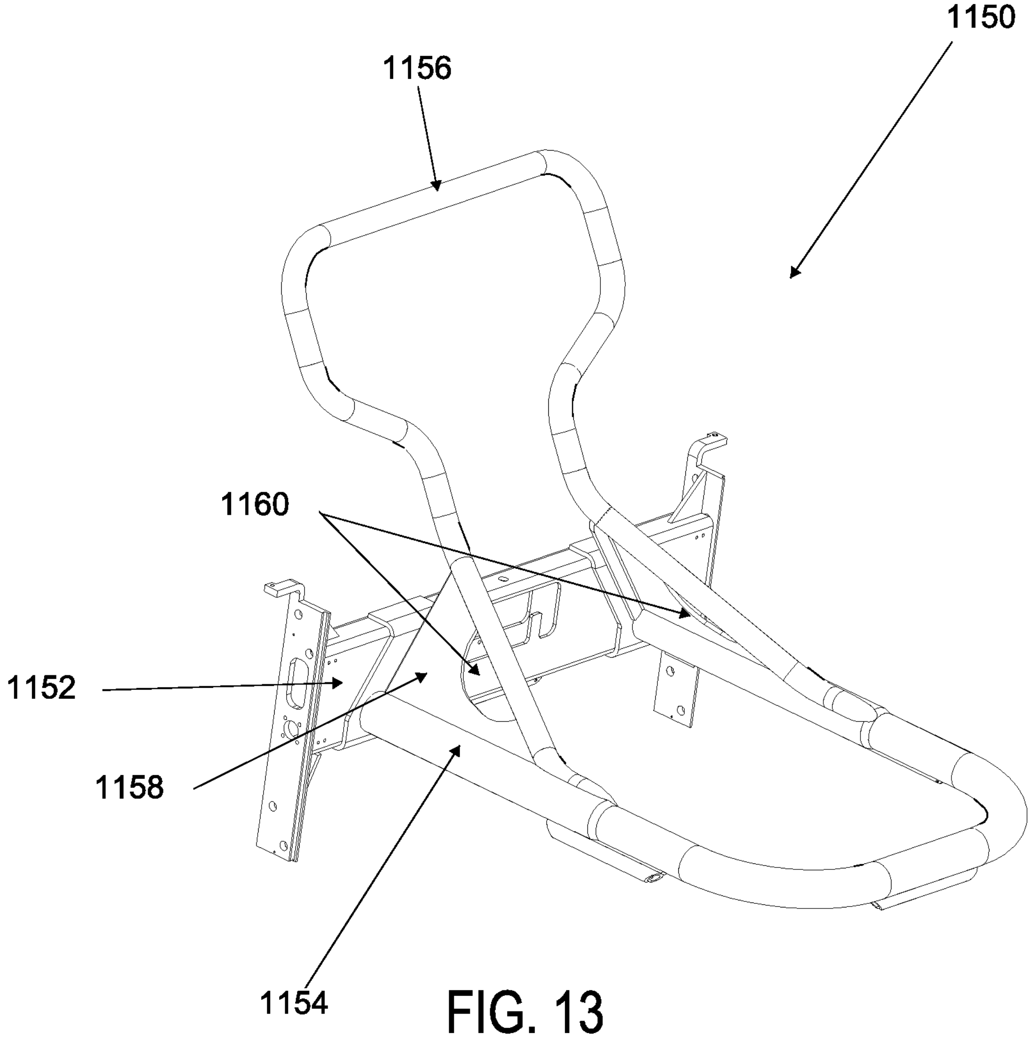
FIG. 13 is a perspective component view of the adjustable assembly of the system in FIG. 11A.

Referring back to FIG. 2A, to improve and/or maintain the sealing between the chamber 310 and the user, the user seal 350 may be supported by seal frame 341. The seal frame 341 may be configured to attach to the chamber 310 about the user seal 350 (or directly to the user seal 350) to resist twisting and/or deformations that may result in air leakage. In the example depicted in FIG. 2A, the seal frame 341 comprises a loop or closed structure attaching to the user seal 350 superiorly. In other examples, the seal frame may comprise an open configuration, or a closed configuration with a detachable segment. While the seal frame 341 may be configured with an orientation lying in a horizontal plane (or at least the lateral 347 and posterior 349 sections of the seal frame 341), in other examples, the seal frame may be oriented in an angled plane, or have a non-planar configuration. The seal frame 341 may also be height adjustable, which may facilitate use of the user seal 350 at a particular body level or body region, but may also provide a limit or stop structure to resist vertical displacement of the chamber, including use of the system by shorter patients. Various examples of height adjustment mechanisms for the seal frame are described in International Patent Application Ser. No. PCT/US2008/011832, which was previously incorporated by reference. In FIG. 2A, the seal frame 341 is attached to a height adjustment bar 352, which in turn is movably supported by two adjustment side posts 354. In other variations, the seal frame may directly interface with the adjustment posts and a height adjustment bar is not used. The configuration and orientation of the seal frame relative to the height adjustment bar 352 and/or the adjustment posts 354 may vary. In the particular example depicted in FIG. 2A, the height adjustment bar 352 and the height adjustment posts 354 are anterior to the seal frame. Also, the anterior seal frame struts 356 are medially oriented with respect to the lateral seal frame struts 358. The medial and anterior attachment between the seal frame 341 and the height adjustment bar 352 may reduce the risk of injury or gait alteration from hand swinging during running or other activities. Furthermore, the seal frame 341 may also have an inferior relationship with respect to the height adjustment bar 352, such that the anterior seal frame struts 356 have a downsloping orientation from an anterior to posterior direction. This downsloping orientation may provide some additional space in the chamber 310 anterior and superior to the user seal 350, which may reduce interference during some activities, including those involving a high-stepping gait (e.g. sprinting or certain high-stepping gait abnormalities). In other variations, however, the seal frame may generally have the same vertical position or higher, relative to the height adjustment bar, and may be attached to the height adjustment bar more laterally or generally flush with the lateral seal frame struts. FIG. 13, for example, depicts a variation of the height adjustment assembly 1150 comprising a height adjustment bar 1152 that is attached to a seal frame 1154 that generally lies in a single plane. the seal frame 1154 is attached to the height adjustment bar 1152 along the lower portion of the bat 1152, which permits the use of the height adjustment bar 1152 to support the attachment of the user seal (not shown) anteriorly. The seal frame 1154 comprises a U-shaped configuration, but in other examples, the seal frame may be Q-shaped or any other shape. In this particular variation, the console frame 1156 is attached to the seal frame 1154 rather than directly to the adjustment bar 1152, but in other variations, may be attached directly to the console frame 1156. One or more support structures 1158 may be provided to support the seal or console frames 1154 and 1156. Here, the support structure 1158 are located at an angle between the seal and console frames 1154 to act to redistribute forces, but may comprise one or more cutouts 1160 to facilitate grasping and movement of the adjustment assembly 1150.

Referring back to FIG. 2A, other structures besides the seal frame 341 may also be attached to the height adjustment bar 352, such as the console frame 331, which may facilitate ease-of-access to the console display and controls with a single height adjustment. As depicted in FIG. 2A, the adjustment assembly 330 comprising the height adjustment bar 352 and the seal frame 341 may further comprise a console frame 331, which may be used to attach the control and visual display of the system 300. This particular example permits simultaneous adjustment of the seal frame 341 and the components of the console frame 331, both of which may be adjusted based upon the height of the user.

Figure 8A:
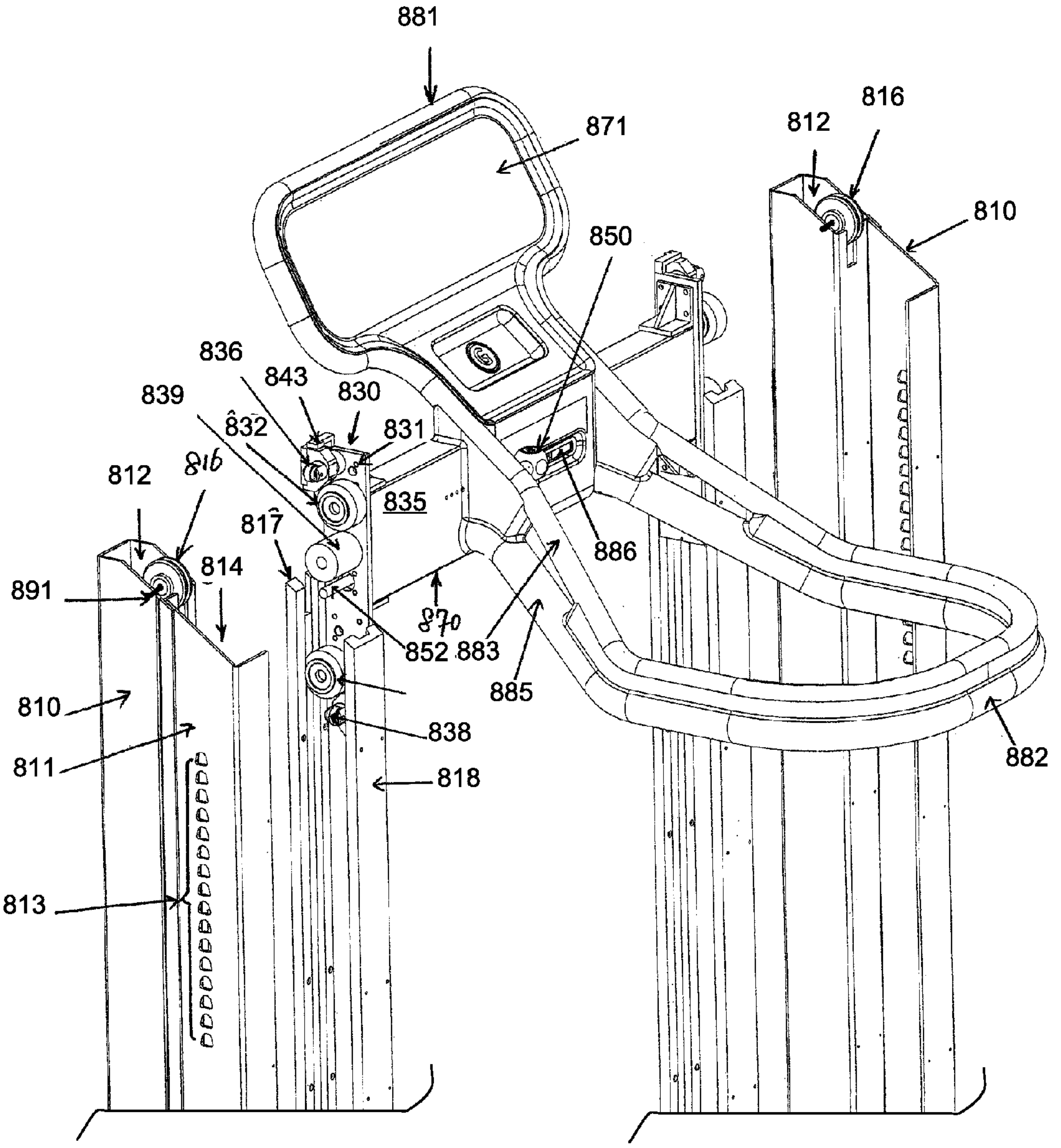
FIG. 8A is a perspective view of one embodiment of a height adjustment mechanism for a differential air pressure system.

FIGS. 8A to 8E further illustrate the structure of the height adjustment mechanism of the DAP system in FIG. 2A. The height adjustment mechanism 800 comprises a pair of generally parallel, vertically oriented side posts 810, a movable assembly 870 with two roller assemblies 830, each of which is at least partially housed inside a side post 810. The movable assembly 870 further comprises a frame 880 and a frame support bar 835 attached to the roller assemblies 830, which movably interface with the two side posts 810. As illustrated in FIG. 8A, the frame 880 further comprises a console portion 881, a seal frame portion 882 and an angled middle portion 883. The angle between the console potion 881 and the seal frame portion 882 may be in the range of about 45 degrees to about 180 degrees, sometimes about 90 degrees to about 135 degrees, and other times about 110 degrees to about 135 degrees. The console portion 881 of the frame 880 may be configured to receive a console tray 871, which may be used to attach and/or support a control panel/display (not shown). The angled middle portion 883 of the frame 880 connects the console portion 881 and the seal frame portion 882. While the frame 880 may be configured to permit height adjustments while grasping or manipulating any portion thereof, in some embodiments, the middle portion 883 of the frame 880 may be configured as a handle to lift or to lower the movable assembly 870. The angled middle portion 883 may provided one or more gripping regions, which may comprise one or more flanges or ridges, for example, and/or be made of a high traction material such as rubber or a block copolymer with polystyrene and polybutadiene regions, e.g., KRATON® polymers by Kraton Polymers, LLC (Houston, Tex.). The middle portion 883 of the frame 880 may be attached to the adjustment bar 835 of the movable assembly 870, which is in turn attached to the two roller assemblies 830 at both of its ends. In some embodiments, the middle portion 883 of the frame 880 may be reinforced by additional bars 885, which may increase the area of the contact surface between the frame 880 and the frame support bar 835 and thereby enhance the structural integrity of the frame 880.

The height adjustment mechanism may further comprise a lift mechanism to at least partially offset the load of the adjustment assembly so that the console portion of the frame may be moved with a reduced weight effect. In some variants, the lift mechanism may provide an offset force that is greater than the load of the movable assembly, which may bias the movable assembly 870 to a higher position. The lift mechanism may comprise springs or pneumatic shock members which apply a vertically upward force on the assembly. The lifting force may be applied directly to the assembly, or indirectly using a pulley system.

In other variations, the system may comprise a counterbalance system which may reduce the risk of sudden drop from inadvertent release of the movable assembly. Movable weights may be provided in the side posts of the system and attached to the movable assembly using a cable or belt with a pulley. Each counterweight may weigh about the half of the weight of the movable assembly, which may reduce the force to the amount required to overcome inertia and/or frictional resistance in order to lower or raise the movable assembly. In some embodiments, the total counterweight may weight slightly less than the movable assembly such that an unlocked movable assembly will be biased to descend until it is locked or it reaches the base of the DAP system. In some variations, the biased descending motion of the movable assembly may be limited by frictional resistance provided by the roller assemblies or other type of mechanism used to restrict the motion of the movable assembly. This design may require a user to apply a force upon the movable assembly to overcome the mass difference between the movable assembly and the counterweight in order to raise the movable assembly. In still other embodiments, the counterweight may weigh slightly more than the movable assembly, thereby biasing an unlocked movable assembly to ascend unless it is locked or the ascending motion of the movable assembly is restricted by the roller assemblies in this specific embodiment. In such embodiment, a user may need to apply additional force to the movable assembly in order to lower its position. In still further embodiments, a compound pulley assembly may be used for a counterweight lighter than the movable assembly and/or to completely offset the weight of the movable assembly.

Figure 8B:
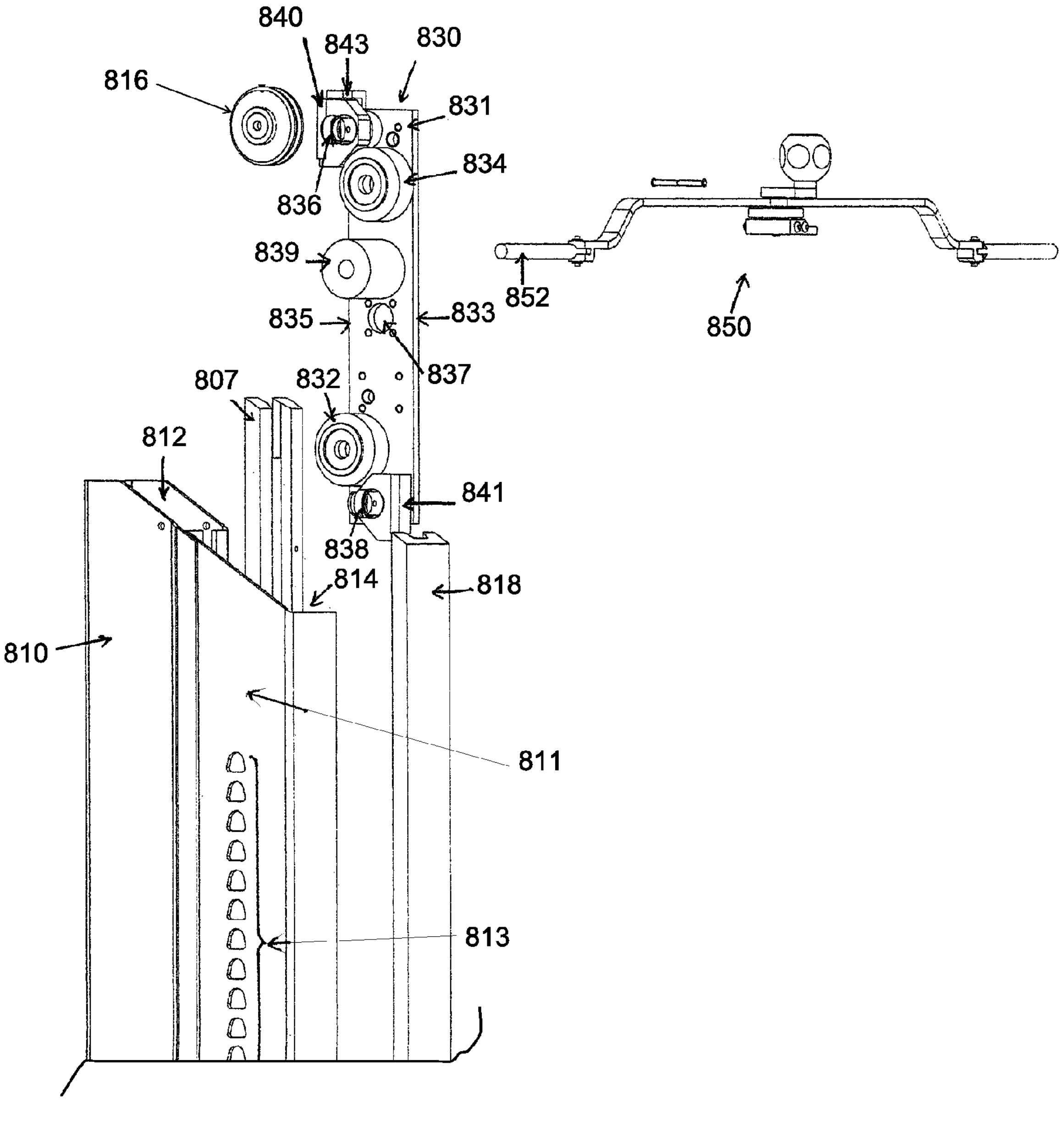
FIG. 8B is a perspective component view of the embodiment form FIG. 8A with two side posts removed to illustrate the components inside the posts.
Figure 8C:
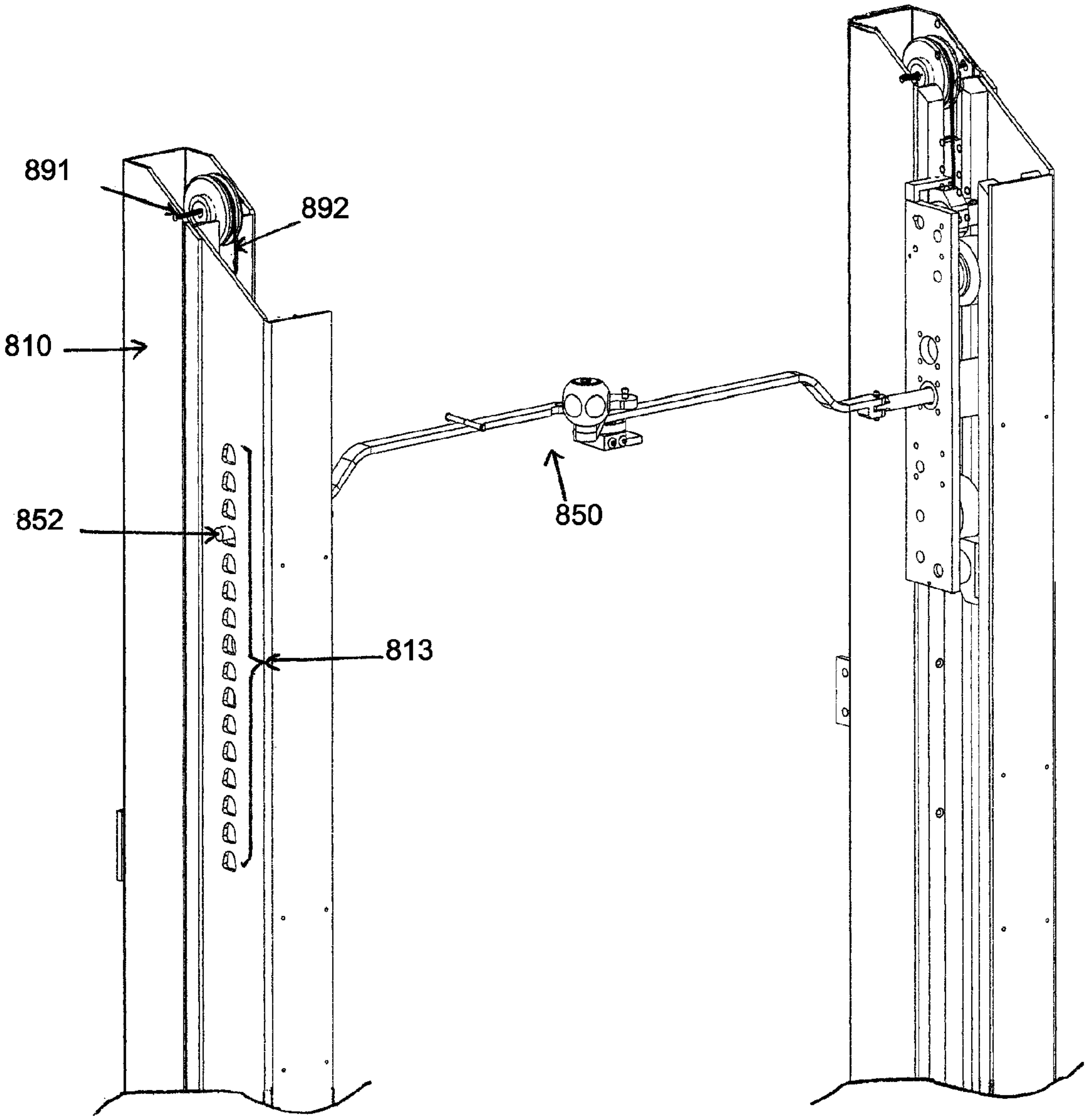
FIG. 8C is a perspective view of the embodiment from FIGS. 8A and 8B in a locked configuration.
Figure 8D:
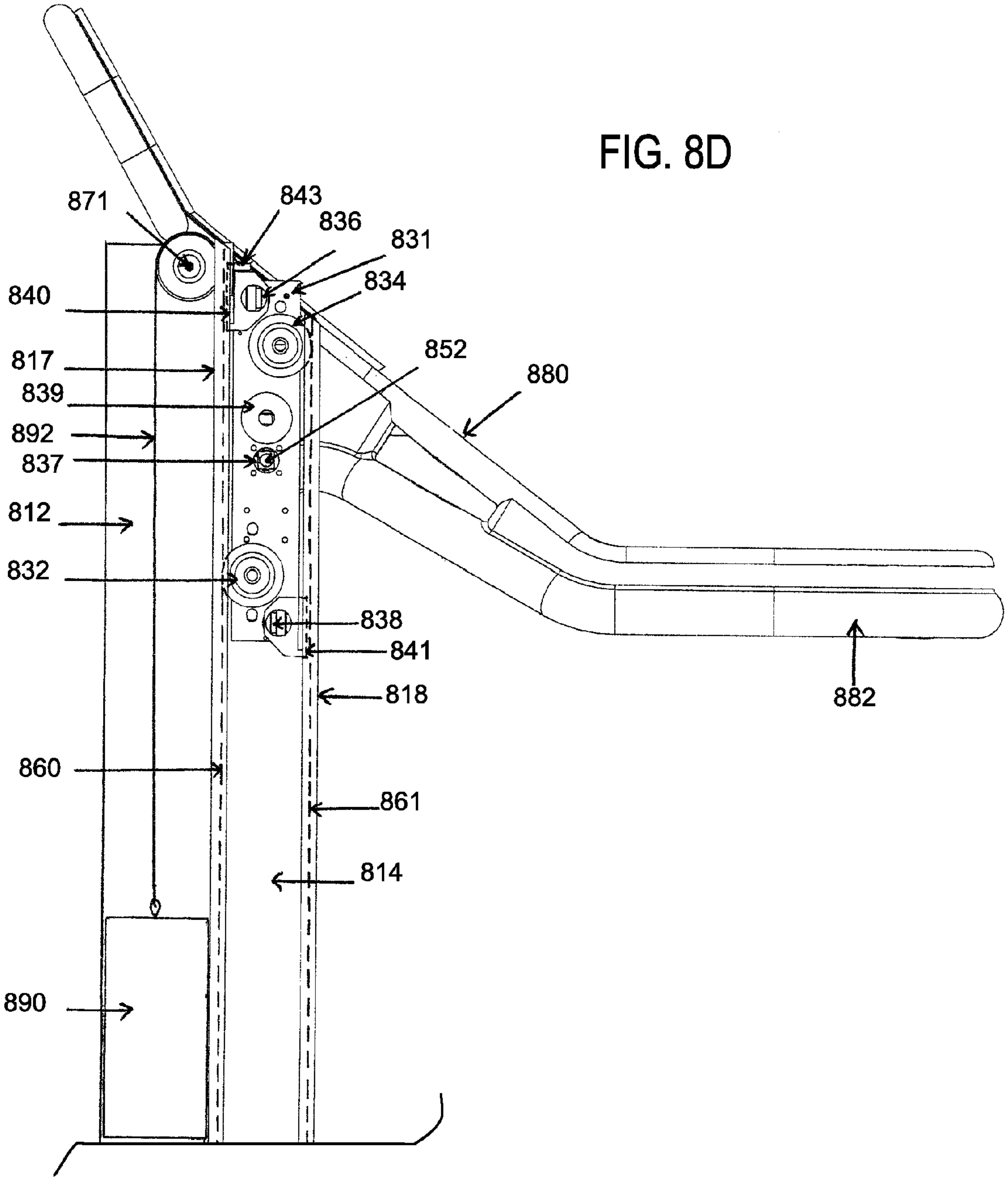
FIGS. 8D and 8E are the orthogonal side view and top view of the embodiment in FIG. 8A, respectively.
Figure 8E:
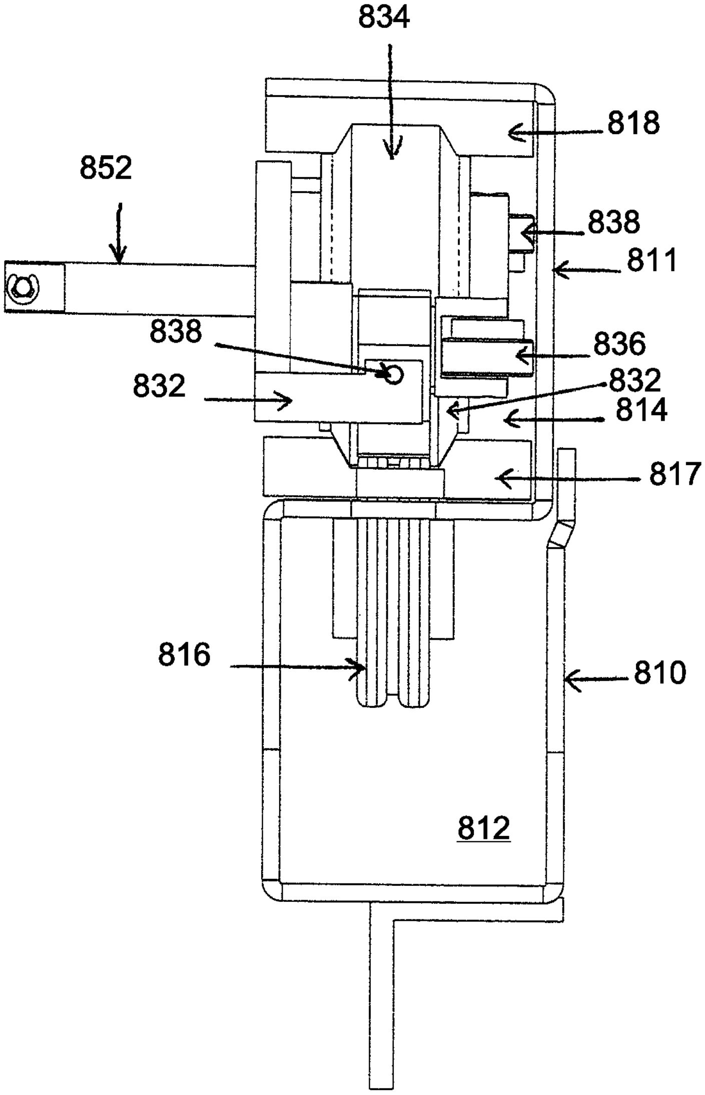

As illustrated in FIG. 8D, each side post 810 may comprise a counterbalance compartment 812 and a roller compartment 814. A pulley 816 is rotatably mounted at the top of the counterbalance compartment 812 around an axial pin 891. The pulley belt or cable 892 is trained over the pulley 816 and one end is connected to a counterweight 890 located in the counterbalance compartment 812. The counterweight 980 is configured to generally move vertically (or other direction of the posts) within the counterbalance compartment 812 of the post 810. The other end of the cable 892 is mounted on a counterweight cable mount 843 located on the top of the roller assembly 830.

As depicted in FIGS. 8A to 8D, the roller assembly 830 may comprise a base plate 831, an anterior roller 834, a posterior roller 832 and two side rollers 836 and 838. In this addition to facilitating the vertical movement of the height adjustment mechanism, the side rollers 836 and 838 may be configured reduce or eliminate the degree of roll of the adjustment mechanism, while the anterior and posterior rollers 832 and 834 may reduce the pitch and/or yaw, which may reduce the risk of jamming. In some variations, the rollers may be directly mounted on the frame support bar 835 and a base plate 831 is not used. The anterior roller 834 is located on the top portion of the base plate 831, near the posterior edge 833 of the base board 831. An anterior roller 834 is located at a bottom portion of the base plate 831 and near the anterior edge 835 of the base plate 831. A superior side roller 836 and an inferior side roller 838 are mounted at the top distal corner and the bottom proximal corner of the base plate 831. Also mounted on the top distal corner and the bottom proximal corner of the base board 831 are two pad structures 840 and 841, which may further align the movement of the roller assembly 830 within the roller compartment 814.

The rollers of the roller assembly may interface with the planar surfaces of the roller compartment, but in the embodiment depicted in FIGS. 8A to 8D, one or more track structures may be provided within the roller compartment to augment the alignment of the roller assembly. The track structures may be integrally formed with the roller compartment surfaces, or may comprise separate structures. For example, referring to FIGS. 8A to 8D, the roller compartment 814 of the side post 810 may comprise an anterior track structure 817 and a posterior track structure 818 in which the anterior roller 834 and the posterior roller 832 movably reside, respectively. These or other track structures may reduce the displacement of the roller assembly 830 in horizontal direction. In some embodiments, one or more of the rollers may be configured with increased frictional rotation resistance, which may reduce the risk of an abrupt descent of the movable assembly. In yet other variations, the tract compartment 814 may comprise tracts or slots to receive the side rollers 836 and 838 of the roller assembly 830. In some embodiments, the inner surfaces of both track compartment 814 and pulley compartment 812 may be coated with one or more lubricants or low friction materials. Also, in other variations, rollers are not provided and movement of the height adjustment mechanism comprises slidable pads coated or covered by low-friction materials and/or low-abrasion materials. In still other variations, the rollers and track structures may be replaced with a rack and pinion configuration.

In some variations, the movable assembly of the DAP system primarily exhibits a vertical motion with respect to the side posts, but in other examples, the movable assembly may comprise a cantilever system which provides some angular or pivot movement that may be used to engage and/or disengage one or more structures of the movable assembly, depending upon the angular position. In some variations, for example, when the movable assembly is being pulled upward by a user located within the loop of the seal frame, the movable assembly may be tilted anteriorly and permits free rotation of the roller structures to raise the movable assembly. When the movable assembly is either pushed downward or is in its base configuration, a relative posterior tilt to the movable assembly may engage one or more resistance or brake pads onto one or more rollers, which may slow or otherwise control the rate of descent. In still other examples, the resistance pads may engage the surfaces of the roller compartment to resist downward/upward movement of the movable assembly.

FIGS. 8A and 8D, for example, depicts pads 840 and 841 mounted about the shafts of the side rollers 836 and 838 in the superior anterior region and the inferior posterior region of the plate 831, respectively. The pads 840 and 841 may be configured to releasably engage the adjacent walls 860 of the posts 810 to resist or slow the movement of the movable assembly 870. In this particular example, the pads 840 and 841 are configured to rotate about the shaft of the side rollers 836 and 838, but in other examples, the pads may have an independent rotatable shaft.

Engagement of the pads 840 and 841 occur when the movable assembly 870 is locked in place with locking pins 852 (which are described in greater detail below) and when the movable assembly is tilted forward (counterclockwise in FIG. 8D). The anterior tilting pushes the pads 840 and 841 against the inner surface of the roller track 814, thereby slowing or even preventing a sudden drop of the movable assembly 870. In some variations, the pads and may be configured to be biased to either the engage or disengaged position, using gravity, springs mechanisms or other force members. Pads 840 and 842 may be made from any suitable materials, such as metal, rubber or plastic.

Figure 15:
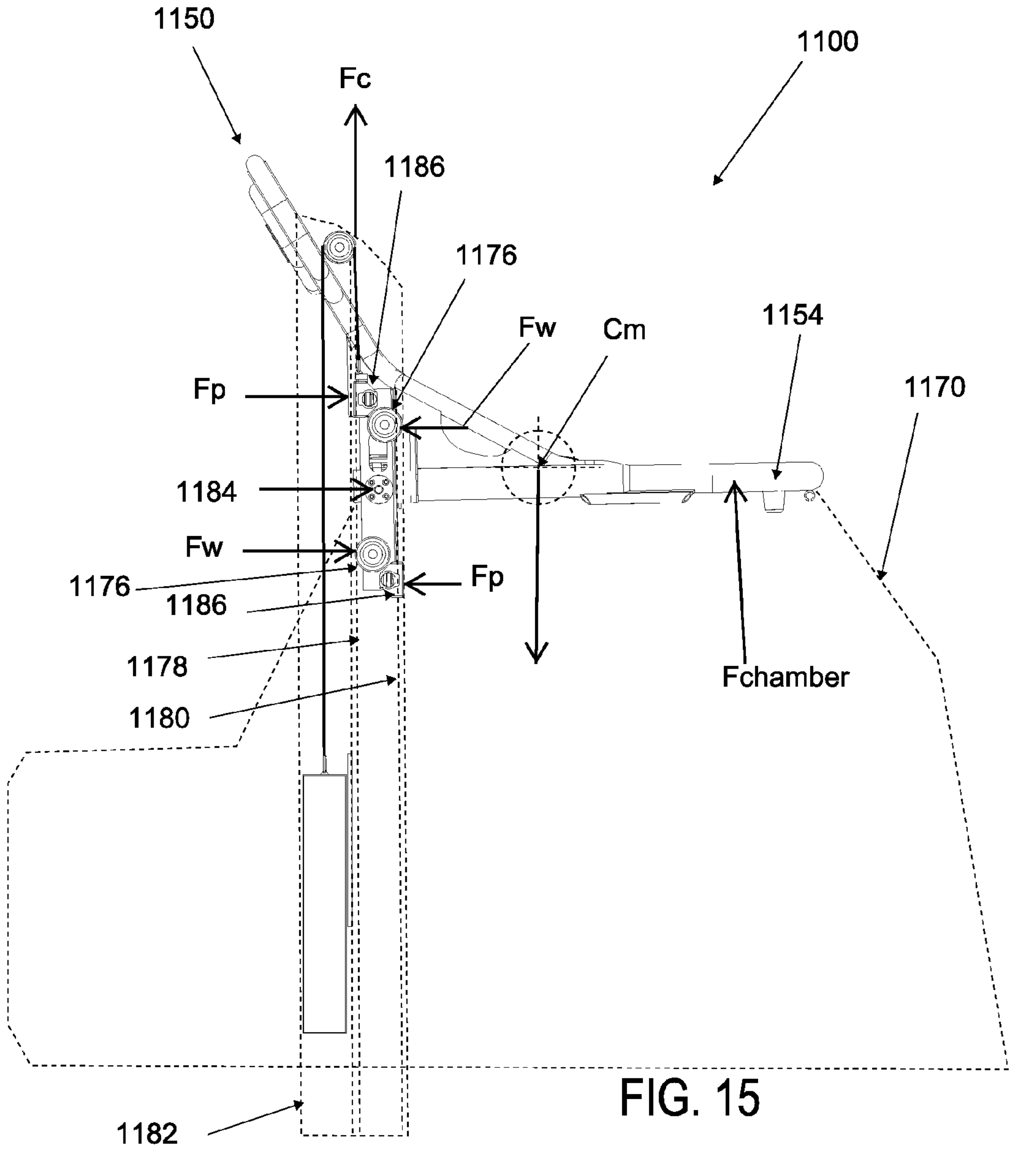
FIG. 15 is a schematic illustration of the forces that may be acting on the adjustment assembly.

In another variation, the cantilever mechanism may be actuated by the inflation or deflation of the chamber attached to the height adjustment assembly. Referring to FIG. 15, which schematically depicts the height adjustment mechanism of 1150 of the DAP system 1100 in FIG. 11A, when the chamber 1170 is unpressurized, the counterbalance system 1172 is configured to balance the weight of the height adjustment assembly 1150 and the effective weight of the chamber 1170 acting on the height adjustment assembly 1150 (which may be less than the actual weight of the chamber 1170). This permits movement ease of movement of the height adjustment assembly 1150 along with the attached chamber 1170. Further, because the center of mass (Cm) of the height adjustment assembly 1150 is posterior to the attachment 1174 of the counterbalance system 1172, the counterbalancing force Fc acts to rotate the height adjustment assembly 1150 in a clockwise fashion, thereby exerting a force (Fw) with the wheels 1176 of the height adjustment assembly 1150 against the walls 1178, 1180 of the adjustment posts 1182 with force Fw). Thus, the height adjustment assembly 1150 can be adjusted without having to overcome gravitational forces and with reduced frictional forces from the wheels engaged to the walls 1178, 1180 of the posts 1182.

When chamber 1170 is inflated, the height adjustment assembly 1152 will begin to lift until its locking pin 1184 engages the next lock opening (not shown), if not already locked. Once locked, the inflated chamber will continue to push the seal frame 1154 and rotate it upwards (or counterclockwise in FIG. 15) around the locking pin 1184. This movement causes the wheels 1176 of the height adjustment assembly 1152 from the walls 1178, 1180 of the adjustment posts 1182 while also engaging the loading pads 1186 to the walls with a pad force (Fp). The pad force Fp may act as a braking force should the locking pin 1184 inadvertently disengage, thereby resisting sudden upward movement of the height adjustment assembly 1152. When system use is completed and the chamber 1170 is depressurized, the pads 1186 will disengage and the wheels 1176 will re-engage the walls 1178 and 1180 of the posts 1182 to facilitate the downward displacement of the height adjustment assembly 1152 to permit the user to exit the system 1100.

In other examples, the pads may be configured to maintain the alignment of the movable assembly rather than braking, and may be coated or covered with low-friction and/or low-abrasion materials. In other examples, the pads may be mounted on the plate separate from the side roller shafts, or configured slide or translate rather than rotate or pivot. In still further examples, the movement of the adjustment assembly and the actuation and release of the locking mechanism, described below, may be motorized. Control of the motorized movement may be performed through the control panel, or with one or more controls provided on the adjustment bar, for example.

Locking Mechanism

A DAP system may also comprise a locking mechanism, which may be configured to adjust and/or lock the position of the height adjustment mechanism. In some embodiments, the locking mechanism further comprises a control interface accessible to the user while using the system. The control interface may comprise an actuator (e.g., a button, a lever, a knob or a switch, etc.). In other embodiments, the control interface may be integrated into the control panel where the user may control and adjust other parameters (e.g., pressure level inside the chamber, parameters of the exercise machine, etc.) of the system.

Referring back to FIG. 2A, the interface of the locking mechanism 333 may comprise a movable lever 345 protruding from a slot 344 located in the adjustment bar 352 of the movable assembly 330. The lever 345 may comprise a locked position which restricts movement of the movable assembly 330 is locked and an unlocked position which permits movement. The locking mechanism 333 may also be configured or otherwise reinforced to also permit movement of the movable assembly 330 using the lever 345 without requiring gripping and manipulation of other movable assembly 330 structures. In some embodiments, a spring or other force mechanism may bias the latch handle 345 to a locked position in order to prevent inadvertent unlocking the movable assembly 330. The movement of the lever 345 is configured to occur horizontally in the embodiment depicted in FIG. 2A, but in other examples, may be configured to move horizontally or some other movement (e.g. rotation). In other variations, other type of locking actuator may be used, such as knobs, slides or buttons, for example. In some instance, a horizontal movement may reduce the risk of inadvertent unlocking, as the motions associated with certain activities, such as treadmill activities, may not typically involve horizontal movements that may inadvertently knock the locking mechanism 333 into an unlocked state. In other embodiments, the locking mechanism may utilize multiple movements different movements (e.g. rotate and pull, or push and pull) to disengage the locking mechanism, which may also reduce the risk of inadvertent unlocking. This may be achieved by adjusting the geometry of the crank linkage mechanism with respect to its angular movement and its linear translation. Additionally the chamber may be shaped to bulge into this area and physically prevent the lever from being unlocked when under pressure. In some examples, a locking sensor may be added to detect the unlocking of the lever prior to full disengagement of the pin. The sensor may have any of a variety of suitable configurations, including those with electrode contact mechanism, push-button mechanism, or magnetic mechanisms, for example.

One example of a locking mechanism that may be used includes a pin-latch locking mechanism where the rotary motion of a control latch may drive linear motion of two locking pins, thereby locking or unlocking the present position of the movable assembly. As illustrated in FIG. 8B, the base plate 831 of the roller assembly 830 may comprises at least one opening 837, which is designed to receive an end pin 852 of a pin-latch locking mechanism 850. The end pin 852 may extend through the opening 837 and engage one of the side recesses or openings 813 on the side post 810, thereby locking the roller assembly 830 and the movable assembly 870 to the post 810. In some examples, the side openings 813 may be protected by a cover to avoid inadvertent push out and disengagement of the locking pin 852. The locking pin 852 may also comprise a notch or groove that forms a mechanical interfit with the openings 813 to further resist inadvertent disengagement. In some embodiments, a tubular pin carrier 839 may be mounted around the opening 837 to guide the end pin 852 and to support the end pin 852 and resist deformation or bending of the pin. The pin carrier 839 may be made from any suitable material, e.g., rubber or metal. In some variations, the distal end of the locking pin 852 may be tapered to decreased the accuracy of aligning the locking pins 852 to the lock openings 837.

Figure 9A:
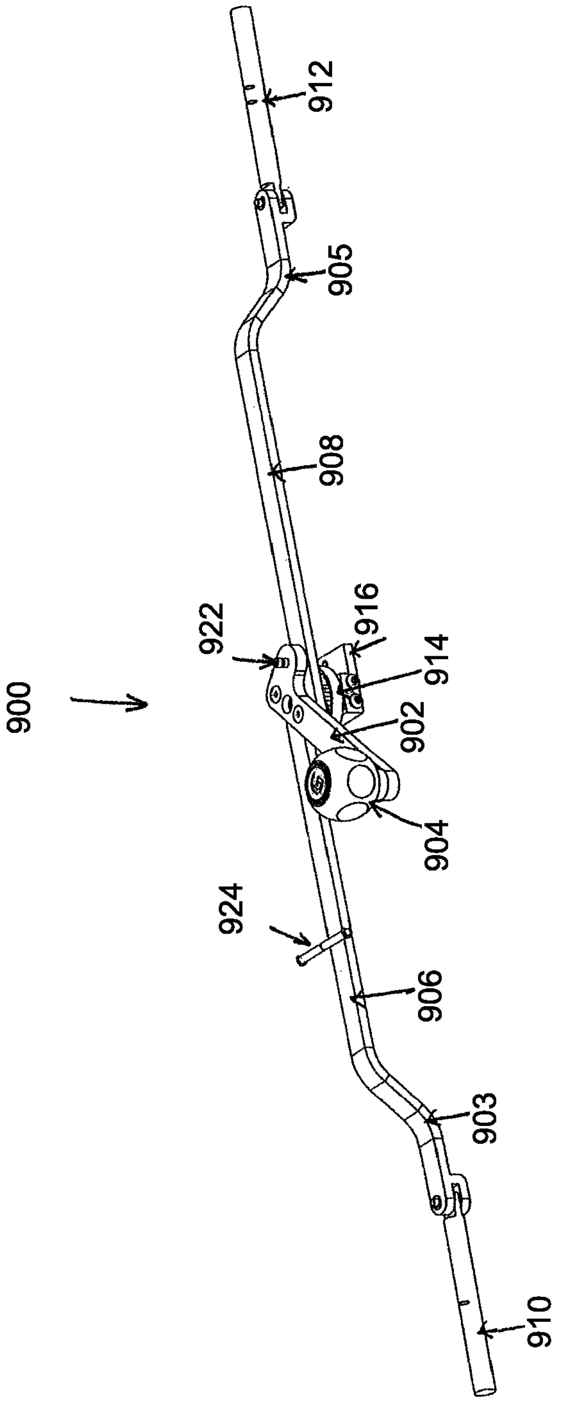
FIG. 9A is a perspective view of one embodiment of a locking mechanism for a differential air pressure system.
Figure 9B:
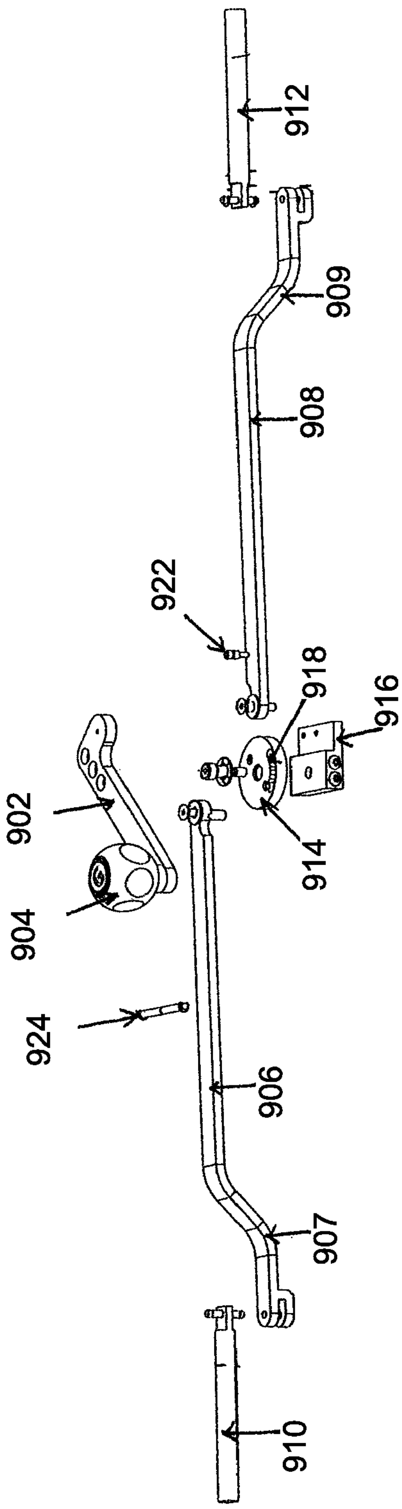
FIG. 9B is a perspective component view of the embodiment from FIG. 9A.
Figure 9C:
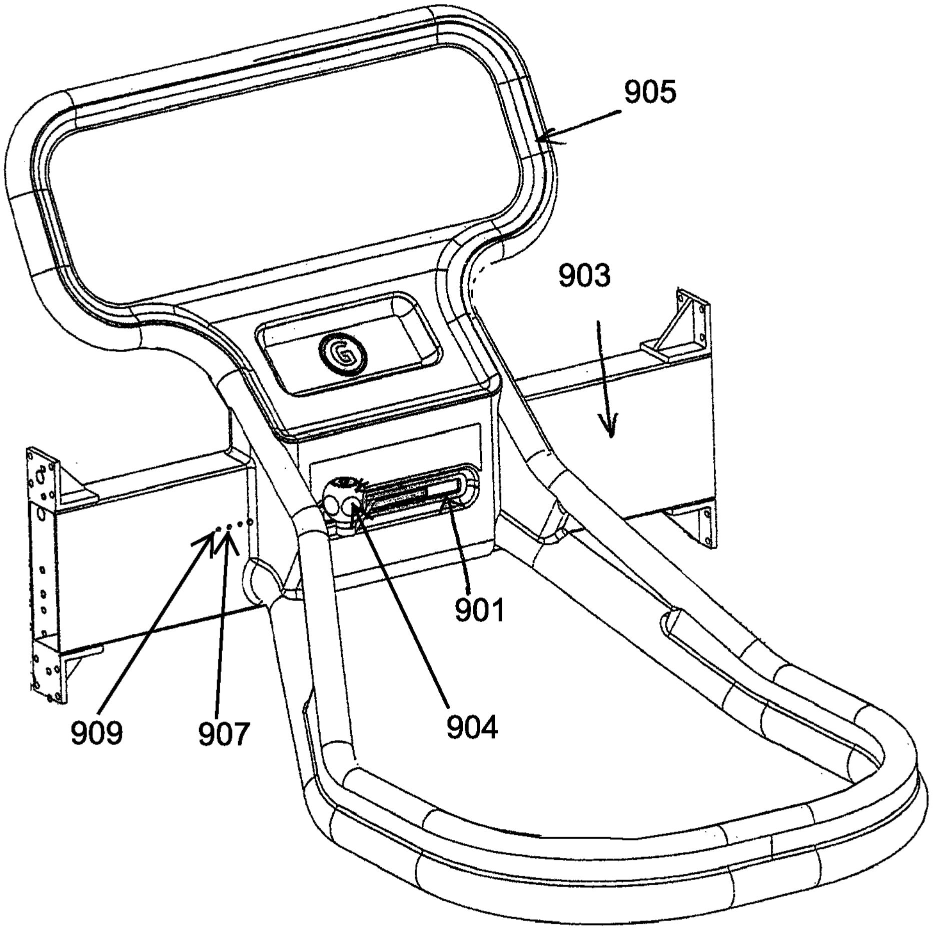
FIG. 9C is a perspective view of the embodiment from FIG. 9A housed in a movable assembly.

As illustrated in FIGS. 9A and 9B, the pin-latch locking mechanism 900 may comprise a drive crank 902, on which a lever handle 904 is attached, two pin-latch rods 906 and 908 and two locking pins 910 and 912, each of which is pivotedly coupled to the end of each pin-latch rod 906 and 908. Both the drive crank 902 and the rods 906 and 908 may be pivotedly fastened to a plate 914, which is mounted on a bottom mount lock 916. There are two symmetrically disposed slots (only one 918 is shown in FIG. 9B) on the plate 914, which provide travel space for the rods' linear motion. In this particular embodiment, when the drive crank 902 is rotated counterclockwise (the range of movement of the drive crank 902 is limited by the front slot 901 in the front tray 903 of the movable assembly 905, as illustrated in FIG. 9C), the two pin-latch rods 906 and 908 are driven to extend outwardly, which in turn push two locking pins outwardly to engage the side openings (e.g., 813 in FIG. 8A) on the side posts, thereby locking the present position of the movable assembly 905. When the drive crank 902 rotates clockwise and moves back to its unlocking position, the rotational motion of the crank 902 retracts the pin-latch rods 906 and 908 inwardly, thereby disengaging the locking pins 910 and 912 from the side openings and unlocking the movable assembly 905.

In some embodiments, the locking mechanism may further comprise a retaining mechanism, which may be used to bias the drive crank 902 to its locking position. In some embodiments, a spring assembly comprising a spring anchor and spring retainer, each of which is attached to one end of a spring, may be used to bias the drive crank 902. FIG. 9A illustrates one embodiment of such spring assembly. As shown in the figure, a spring retaining pin 922 is pivotedly attached to the drive crank 902. A spring anchor pin 924 may engage the frame support bar 835 of the movable assembly 870 depicted in FIG. 8A, thereby anchoring one end of the spring (not shown) to a fixed position. The distance between the anchor pin 924 and the retaining pin 922 may be larger when the lever 904 is placed in its locking position than the distance between the two pins when the ball 904 is paced in its unlocking position, the spring is charged with potential energy when the lever 904 is placed at the right end of the front slot 901, i.e., its locking position, The charged spring may exert a counterclockwise retaining force on the drive crank 902, thereby biasing the drive crank 902 to its locking position. In some of these circumstances, in order to unlock the movable assembly 905, a user may need to apply an external clockwise rotational force on the drive crank 902 to overcome the biasing force from the charged spring. Thus, inadvertent unlocking of the movable assembly may be reduced or avoided. The biasing force provided by the spring (or other bias member) may be adjusted by adjusting the position of the anchor pin 924. As illustrated in FIG. 9C, the front tray 903 of the movable assembly 905 may comprise more than one anchor pin holders 907 and 909. For example, if the anchor pin 924 is placed into the far left pin holder 909, the retaining spring will be charged to a higher degree compared to the case where the anchor pin 924 is placed into the opening 917, thereby exerting a higher retaining force on the drive crank 902. It is noted that affixing the spring anchor pin to the console front tray 903 is not necessary. In some embodiments, the spring anchor pin may be affixed to another structure, the board 831 of the roller assembly, for example. The relative location of the spring anchor pin 924 and spring retaining pin 922 (e.g., the anchor pin 924 is disposed to the left of the retaining pin 922 in this specific embodiment) may vary. For example, if a crank with different geometric configuration is used, the locking mechanism may comprise locking and unlocking positions opposite to those of current embodiment shown in FIGS. 9A to 9C (e.g., a user may rotate the control crank 902 counterclockwise in order to unlock instead) . In such a case, the spring anchor pin 924 may be placed to the right of the spring retaining pin 922 in order for the spring to bias the control crank 902 to its locking position. One of skill in the art will understand that any of a variety of linkage mechanisms may be used, such as the locking wheel mechanisms used for bank vaults and port doors on ships. Also, the direction of movement of the lever may be configured for any of a variety of directions and movements, both linear and non-linear, and vertical and horizontal.

The pin-latch locking mechanism may comprise numerous features to facilitate engagement the locking pins to a pair of side openings. For example, providing two pivotably movable end locking pins 910 and 912 to the two pin-latch rods 906 and 908 may reduce the torquability of the pin-latch system, therefore enhancing the flexibility and steerability of the system. In some embodiments, the end pins 910 and 912 may be made from a same material as the pin-latch rods 906 and 908. In other embodiments, the pivotable end pins 910 and 912 may be made from a more elastic material than the rods 906 and 908, thereby making them more steerable. As a result, it may be easier for such end pins to engage side openings on the side post. In some embodiments, a pin cover, e.g., the tubular structure 839 in FIG. 7B, may be used to guide the linear motion of the end pin, which may further facilitate the engagement of the end pin 910 and 912 to the side openings. In some embodiments, the end portion 903 and 905 of the two rods 906 and 908 may comprise an elastic material to further reduce the torquability of the locking mechanism. In some situations, a user may try to lock the movable assembly when the locking pins 910 and 912 fail to engage a pair of side openings. User's such operation may cause stress and/or stain in the pin-latch rods 906 and 908. In some embodiments, end portions 903 and 903 may comprise a curved configuration (e.g., "S"-shape) that may help reduce such stress or strain since it gives room for end pins 910 and 912 to retract when they fail to engage.

Figure 12:
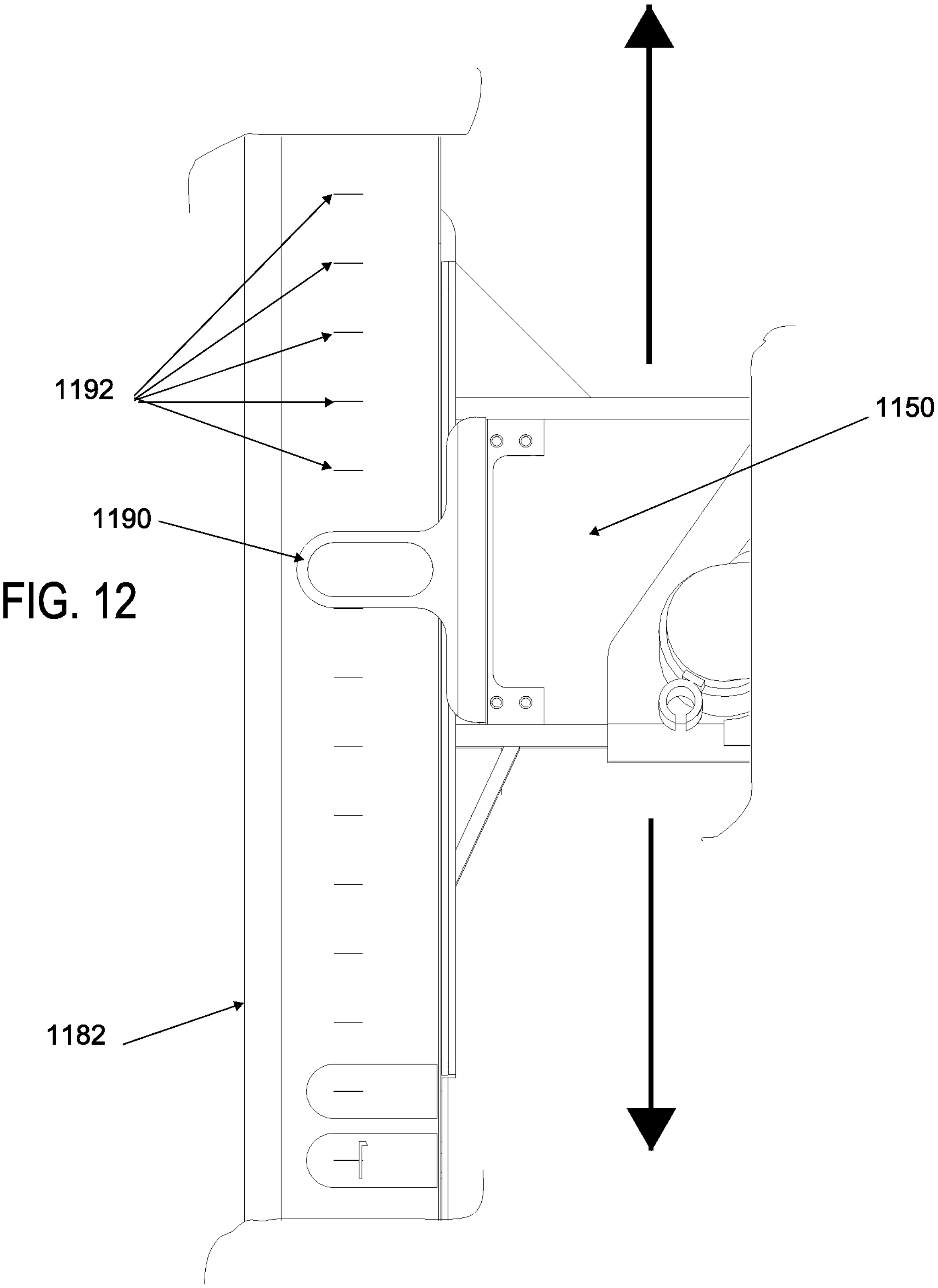
FIG. 12 is a posterior elevational view of the height indicator of the adjustable assembly in FIG. 11A.

To facilitate the setting and locking of the movably assembly at the desired level, the DAP system may provide indicia on the system to guide or suggest a position based upon the user's height. In FIG. 12, for example, the height adjustment assembly 1150 of the DAP system 1100 includes a movable indicator pointer or opening 1190 which overlies the side post 1182. The side post 1182 includes a series of indicia 1192 (e.g. heights in feet/inches or centimeters) which may be used as a guide for the adjustment of the movable assembly 1150. The indicia 1192 may be printed on the side post 1182 or provided as an LCD or LED display along the post 1182. In other variations, for privacy, the user's height may be entered into the control panel (not shown) one or more lights from a column of lights may be selectively activated based upon the user's height input to indicate the suggested position of the movable assembly 1150. In still other variations, the control panel and/or or the movable assembly may provide auditory, visual or tactile signals to the user indicative of correct positioning, or indicative of instructions to move the assembly up or down, for example.

Attaching the Chamber to the Movable Assembly

As noted above, the height of the user seal and the movable assembly may be adjusted simultaneously. One way to implement this feature is to attach a portion of the chamber of a DAP system to a portion of movable assembly so that the height of the user seal may be adjusted by the vertical movement of the movable assembly. Such designs may simplify the height adjusting operation by allowing the user to adjust the height of the control panel and the user seal in a single step. Further, restricting relative motion between the pressure chamber and the frame may stabilize the user seal against a user's body, which, in turn may help maintain the seal between the user and the chamber. The frame 880 may be attached to the chamber in a variety of ways. As one example, the proximal portion 882 of the frame 880 may be entirely or partially covered with one or more fabric loops, which may further attach to the chamber material around the user seal by adhesive or VELCRO™ type of fastener, and/or a zipper for instance. In other embodiments, the top chamber section may comprise one or more magnets that may attract the frame 880 if the frame 880 is made from metal.

Figure 10A:
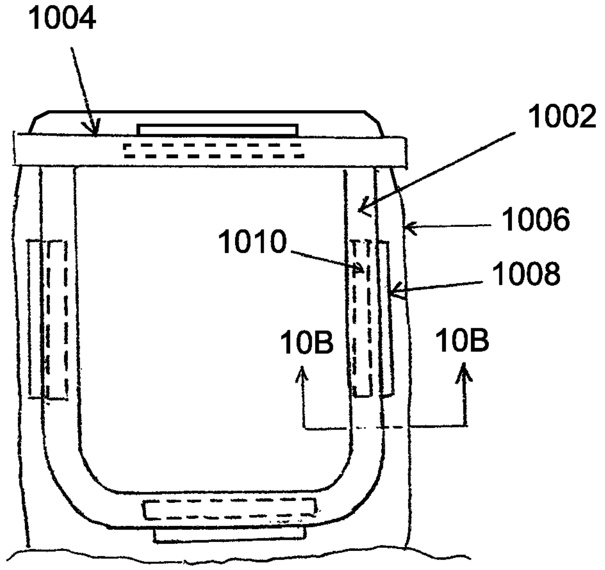
FIGS. 10A and 10B are schematic illustrations of one embodiment of a method to attach an inflated chamber to a portion of a console frame.
Figure 10B:
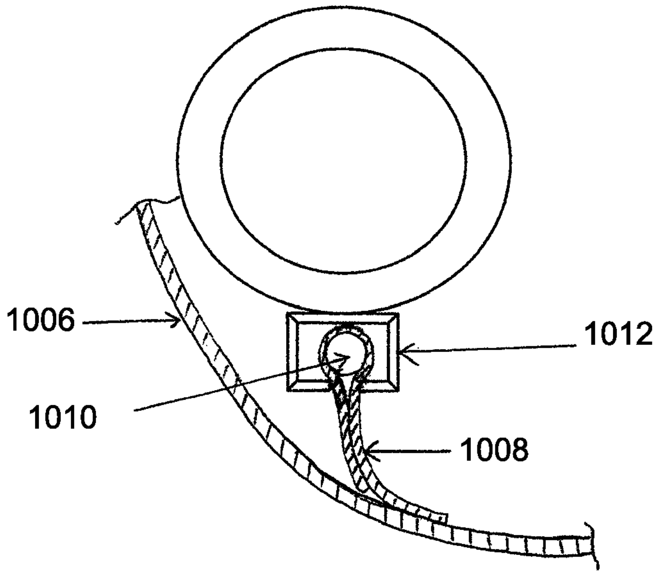

FIGS. 10A and 10B schematically illustrate another attachment mechanism of an inflatable chamber 1006 to a proximal loop 1002 of a frame 1004. As illustrated in FIG. 10B, a tension loop 1008 used to attach to a portion of an inflatable chamber 1006 may be placed around an elongate rail 1010, which is contained in an elongate slotted retention channel 1012 fixedly mounted underneath a portion of the loop 1002. The rod 1010 may have a larger diameter than the width of the longitudinal slot so that the rod may move within the retention channel 1012 but may not be removed from the slot even if the chamber 1006 is tensioned. The slotted retention channel 1012 may or may not comprise the same length as the rail 1010. In some variations, a plurality of tension loops may be used to attach the chamber to the console frame 1004. The tension loop may or may not be made from the same material as the inflatable chamber. The tension loop may be attached to the chamber by adhesive, VELCRO™ type of fasteners, fastening buckles, buttons or other types of suitable attachment method. In some examples, the attachment of chamber to the user frame facilitates the raising and/or lowering of the chamber with the movable assembly, but may also maintain the geometry of the chamber in the region of the user seal, which may reduce the frequency and/or magnitude of air leaks out of the seal.

In some variations, the seal frame and the chamber may be configured so that the seal frame remains inferior to the user seal, which may provide room for a user's arm swing or other types of upper body motion. In other variations, the user seal may be substantially flush with the proximal loop of the console frame such that the lower body (e.g., legs or hip) of a user will not collide with the console frame when the user is running or otherwise moving the user's lower body. In some embodiments, the protruding structure formed by the user seal above the console frame loop may comprise a cylindrical configuration, whereas in other embodiments, such structure may comprise a frustum-conical configuration if the user seal is formed by a piece of stretchable flap. The dimension of the proximal loop of the movable assembly may be larger than the user seal in a chamber (e.g., see FIG. 2B), while in other embodiments, the proximal loop may be smaller. In some embodiments, the average distance between the inner surface of the proximal loop and the outer edge of the user seal may be in the range of about 0 cm to about 20 cm or more, other times about 2 cm to about 10 cm, and other times about 1 cm to about 5 cm.

The frame assembly comprises various structures to support and/or stabilize other structures of the DAP system. For example, the frame assembly may comprise a platform or base to attach the inflation chamber, as well as bars, braces or rails that limit the shape the inflation chamber. The frame assembly may also used to stabilize the height adjustment mechanism, using various frame structures to dampen vibrations or stabilize other stresses generated by or acting on the DAP system or the user during use. In the example depicted in FIGS. 2A to 2C, the DAP system 300 comprises a frame assembly 320 with a base 321, side hand-rails 322, a front horizontal bar 323 and front vertical bars 324. Some portions of the frame assembly 330 may also maintain or limited the chamber to a predetermined shape. For example, when chamber 310 is inflated, the expansion of the chamber 310 at the front end of the system 300 is limited by side bars 325, L-shape bars 326, and the front bar 327 of the front brace 324. The lateral expansion of the chamber 310 may be limited by the rear hand-rails 322. The rear hand-rails 322 may provide support to a user during exercise and/or in the event of pressure change within the chamber 310, which may cause the user to lose body balance temporarily. In some embodiments, a pressure source may be placed upon or mounted to the two L-shape bars 326. In one example, the pressure source may be a blower. The pressure source may be placed at other locations as well. For example, it may be placed on the ground next to the DAPS to reduce vibration that may be caused by the pressure source.

The frame assembly 320 may be assembled together by any suitable methods known to the ordinary skilled in the art. Non-limiting examples include brackets, bolts, screws, or rivets. In some embodiments, in addition to or in lieu of the components described above, the frame assembly 320 may comprise other components or parts. For examples, additional bars or braces may be used to stabilize the system 300 while the user is in motion.

In other examples, one or more other structures may be attached to the frame assembly to facilitate certain types of exercise or training. For example, the adjustment mechanism may further comprise a walker or cane mechanism to simulate, facilitate or coordinate upper body lifting and planting motions associated with walker or cane use. In some examples, the walker or cane mechanism may incorporate sensors which may be synchronized to the treadmill or other exercise machine used with the DAP system. In still other examples, one or more panels of the chamber may be sealably opened to permit access to the enclosed portions of the body. Also, in further examples, the chamber and/or the frame assembly, or may include harnesses or straps to provide non-pneumatic body support.

As noted above, the expansion of the chamber 310 in the embodiment depicted in FIGS. 2A to 2C may be limited by several bars, rails and/or braces of the frame assembly 320 of the DAP system 300. In this specific embodiment, the two parallel height adjustment mechanisms 334 may also facilitate shaping the inflated chamber by limiting its lateral expansion. As illustrated in FIG. 2A, the vertical expansion of an inflated chamber 310 around a user seal 350 may be limited by a console frame 331 of the movable assembly 330. When a user is positioned in the inflated chamber 310 while using the system 300, the seal frame 341 of the movable assembly 330 may be disposed just at or above the user's waistline. As best illustrated in FIG. 2B, the seal frame 341 of the movable assembly 330 may be of approximately the same width as the top section 313 of the chamber 310, but may be slightly wider than the user seal 350. As a result, when chamber 310 is inflated, the disposition of the console frame may allow the user seal 350 to rise but depress bulging chamber material around the seal 350. This design may prevent or reduce the risk that the bulging chamber material around the user seal 350 from interfering with the user's upper body motion and allow the user to swing arms freely and comfortably. As will be discussed in further detail below, the top section 313 of the chamber 310 may be attached to the a portion of console frame 331, thereby allowing the height of user seal 350 to be adjusted with the height of movable assembly 330.

In addition to the structures that have been described here, additional structures may be used to limit the expansion of the chamber 310 in order to contour the chamber to a specific configuration. For example, X-shape cross-bars may be added between the height adjustment mechanism 334 and the rear hand-rails 322 to flatten the bulging chamber material on the sides of the base. In some embodiments, the chamber 310 may comprise one or more rigid portions or other types of integrated supporting structures that may facilitate maintaining the inflated chamber in a particular configuration or shape.

As described previously, the DAP system may further comprise one or more panels or end caps attached to the frame assembly or other structures of the system. For example, The DAP system 1100 in FIG. 11 comprises a side post panel 1102 may be attached to the side posts 1104 to protect the lock openings of the locking mechanism (e.g. openings 813 of the post 810 in FIG. 8A) from inadvertent disengagement from external bumping, or from inadvertent pinching of clothing or other objects between an exposed locking opening and an exposed locking pin when the locking mechanism is engaged. Side frame panels 1106 and anterior panels 1108 may be removable attached to the frame 1110. These panels 1106 and 1108 may protect users from the mechanical and electrical components of the system 1100 as well as protecting the system components from damage.

Use of the Embodiment Described Above

Described herein are various embodiments of a DAP system equipped with a height adjustment mechanism that allows a user to adjust the height of the user seal in an effortless and a user friendly manner. Further, the DAP system also comprises a locking mechanism configured to be used in conjunction with the height adjustment mechanism also in a graceful manner. In some embodiments, a user may be able to complete the adjusting step and the locking step with a single hand. As in one embodiment, after a user finishes a session using a DAP system as illustrated in FIG. 3A, the user may first stop the exercise machine and then instruct the processor to stop pressurizing or maintaining the elevated pressure level within the pressure chamber. This can be done through the user interface system (e.g., a control panel). The user may release the user seal from the user's body and then unlock the movable assembly by rotating the latch ball to its unlocking position (e.g., counterclockwise rotation in this specific embodiment). Because of the use of counterbalancing system in this embodiment, lowering the movable assembly does not require the user to apply a large force. As a result, the user may use the hand that operates the latch ball to press down the console frame in order to lower the movable assembly.

Descending of the movable assembly presses the top chamber section, therefore deflating the chamber. As discussed in detail above, the chamber with multiple fold-lines may deflate in a pre-determined fashion and facilitate the user stepping out of the chamber with ease. Once the chamber is completely deflated, the user may step out of the chamber. The movable assembly that is biased by its gravity may stay on top of the folded chamber.

The next user of the DAP system may first step into the console frame and the opening of the user seal in the top section of the chamber and place the user seal around the user's waistline. Then the user may communicate with the DAP system processor through the user interface system to actuate the inflation of the chamber. Once the inflation begins, the user may lift the movable assembly to a position where the user feels that the height of the user seal is proper. As discussed above, because of the counterbalancing design in this embodiment, the user may only need to apply a small force in order to lift the movable assembly. As a result, the user may complete the lifting and locking of the consoles assembly with one hand. After the user locks the position of the movable assembly, the user may start using the exercise machine.

Although the embodiments herein have been described in relation to certain examples, various additional embodiments and alterations to the described examples are contemplated within the scope of the invention. Thus, no part of the foregoing description should be interpreted to limit the scope of the invention as set forth in the following claims. For all of the embodiments described above, the steps of the methods need not be performed sequentially. Accordingly, it is not intended that the invention be limited, except as by the appended claims.

What we claim is:

1. A differential air pressure system, comprising:

a positive pressure chamber with a seal interface configured to receive a portion of a user's body and form a seal between the user's body and the chamber;

a height adjustment assembly attached to the chamber adjacent to the seal interface; and a control panel attached to the height adjustment assembly.

2. The system of claim l, wherein said positive pressure chamber comprises at least one transparent panel.

3. The system of claim 2, wherein said positive pressure chamber comprises a plurality of transparent panels.

4. The system of claim 1, wherein said positive pressure chamber comprises a slip resistant panel.

5. The system of claim 4, wherein said slip resistant panel is adjacent to the seal interface.

6. The system of claim 2, wherein the height adjustment assembly comprises a horizontally actuated locking mechanism.

7. The system of claim 2, wherein said height adjustment assembly comprises two movable ends located within two corresponding adjustment posts.

8. The system of claim 7, wherein each movable end comprises at least two rollers.

9. The system of claim 8, further comprising a first roller that is orthogonally oriented with respect to a second roller.

10. The system of claim 8, wherein each movable end comprises at least one movable braking pad.

11. The system of claim 10, wherein at least one movable braking pad may be actuated by tilting the height adjustment assembly.

12. The system of claim 11, wherein said height adjustment mechanism further comprises a counterbalancing system configured to at least partially offset the weight of said movable assembly.

13. The system of claim 12, wherein said counterbalancing system comprises a weight located at least one adjustment post.

14. The system of claim 1, further comprising a platform attached to the chamber using a seal mechanism.

15. The system of claim 14, wherein the seal mechanism is configured to increase sealing to the platform with increased pressure within chamber.

16. The system of claim 14, wherein the sealable mechanism further comprises a foam member.

17. The system of claim 2, further comprising a pin latch locking mechanism configured to lock the present position of said user seal.

18. A differential air pressure system, comprising:

a pressure chamber; and a vertically adjustable cantilevered frame having a first movable configuration and a second locked configuration wherein the second locked configuration is actuated by the pressure chamber.

* * * * *